United States Patent
Nagahara et al.

(10) Patent No.: US 10,011,681 B2
(45) Date of Patent: Jul. 3, 2018

(54) PROCESS FOR PRODUCING A LACTIC ACID-GLYCOLIC ACID COPOLYMER OR A SALT THEREOF

(71) Applicant: MITSUI CHEMICALS, INC., Minato-ku, Tokyo (JP)

(72) Inventors: Kiyoteru Nagahara, Omuta (JP); Yasushi Fukuiri, Miyama (JP); Tomoyuki Kawabata, Ise (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 153 days.

(21) Appl. No.: 14/782,145

(22) PCT Filed: Apr. 8, 2014

(86) PCT No.: PCT/JP2014/060158
§ 371 (c)(1),
(2) Date: Oct. 2, 2015

(87) PCT Pub. No.: WO2014/168134
PCT Pub. Date: Oct. 16, 2014

(65) Prior Publication Data
US 2016/0060388 A1    Mar. 3, 2016

(30) Foreign Application Priority Data

Apr. 11, 2013  (JP) .................................. 2013-082988
Feb. 5, 2014  (JP) .................................. 2014-020184

(51) Int. Cl.
C08G 63/90 (2006.01)
C08G 63/06 (2006.01)
A61K 47/34 (2017.01)

(52) U.S. Cl.
CPC .............. *C08G 63/90* (2013.01); *A61K 47/34* (2013.01); *C08G 63/06* (2013.01)

(58) Field of Classification Search
None
See application file for complete search history.

(56) References Cited

U.S. PATENT DOCUMENTS

| 4,810,775 A | 3/1989 | Bendix et al. |
| 5,585,460 A | 12/1996 | Yamada et al. |
| 9,187,593 B2 | 11/2015 | Dadey et al. |
| 2003/0153724 A1 | 8/2003 | Yamamoto et al. |
| 2004/0241229 A1 | 12/2004 | Yamamoto et al. |
| 2005/0238618 A1 | 10/2005 | Huang |
| 2006/0128938 A1 | 6/2006 | Yamamoto et al. |
| 2007/0259036 A1 | 11/2007 | Yamamoto et al. |
| 2008/0108778 A1 | 5/2008 | Yamatomo et al. |
| 2010/0292195 A1 | 11/2010 | Dadey et al. |
| 2011/0144301 A1 | 6/2011 | Enderle et al. |
| 2011/0207834 A1 | 8/2011 | Kim et al. |
| 2012/0295848 A1 | 11/2012 | Yamamoto et al. |

FOREIGN PATENT DOCUMENTS

| JP | 63-254128 A | 10/1988 |
| JP | 4-218528 A | 8/1992 |
| JP | 8-245779 A | 9/1996 |
| JP | 2000-026588 A | 1/2000 |
| JP | 2003-026790 A | 1/2003 |
| JP | 2004-155792 A | 6/2004 |
| JP | 2007-534803 A | 11/2004 |
| JP | 3902518 B2 | 4/2007 |
| JP | 2009-525372 A | 7/2009 |
| JP | 2010-519218 A | 6/2010 |
| JP | 2010-180145 A | 8/2010 |
| JP | 2011-178729 A | 9/2011 |
| JP | 2012-508293 A | 4/2012 |
| JP | 5046447 B2 | 10/2012 |
| JP | 50446447 B2 | 10/2012 |

OTHER PUBLICATIONS

International Search Report (PCT/ISA/210) dated Jun. 24, 2014, by the Japanese Patent Office as the International Searching Authority for International Application No. PCT/JP2014/060158.
Office Action issued by the Japanese Patent Office in corresponding Japanese Patent Application No. 2015-511260 dated Apr. 5, 2016 (3 pages).

*Primary Examiner* — Rachel Kahn
(74) *Attorney, Agent, or Firm* — Buchanan, Ingersoll & Roonery PC

(57) ABSTRACT

Provided is a purified lactic acid-glycolic acid copolymer, preferably in the form of powder, having a reduced content of dimers such as residual lactide and glycolide that can be produced by a simple industrial process without the use of any high-shear special device. Further provided is a high-purity lactic acid-glycolic acid copolymer which has small amounts of dimers such as residual lactide and glycolide and small amounts of a low-molecular weight lactic acid-glycolic acid copolymer or a salt thereof and which has a small ratio of weight average molecular weight to number average molecular weight (Mw/Mn). The copolymer can be produced in accordance with a defined process.

16 Claims, No Drawings

PROCESS FOR PRODUCING A LACTIC ACID-GLYCOLIC ACID COPOLYMER OR A SALT THEREOF

TECHNICAL FIELD

The present invention relates to processes for producing a lactic acid-glycolic acid copolymer or a salt thereof.

BACKGROUND ART

Lactic acid-glycolic acid copolymers or derivatives thereof such as salts are known as biodegradable polymers and are useful as, for example, materials for sustained release microcapsules for containing physiological active substances. If lactic acid-glycolic acid copolymers used as sustained release formulation materials contain large amounts of lactide and glycolide used as raw materials, these residual materials are hydrolyzed to form acids, which promote the decomposition of the lactic acid-glycolic acid copolymers. Consequently, the sustained release formulations fail to achieve the desired sustained release period. For example, known techniques for producing purified lactic acid-glycolic acid copolymers suited for sustained release formulations are 1) to add water to a solution of a polyhydroxycarboxylic acid in a hydrophilic organic solvent to precipitate a copolymer (Patent Literature 1), 2) to treat a polyester solution in the presence of a precipitation solvent with a high-shear device to produce a copolymer as fine particles (Patent Literature 2), 3) to supply a solution of a polyhydroxycarboxylic acid in an organic solvent and isopropyl alcohol to a device having a kneading mechanism, and to perform operations so as to produce a powdery copolymer (Patent Literature 3), and 4) to treat a lactic acid polymer in the presence of a solvent having a lactide solubility of not less than 4% while performing crushing and stirring with a mixer and thereby to extract residual lactide (Patent Literature 4). However, the purified polymer obtained by the method 1) is a viscous liquid that contains a relatively large amount of the organic solvent remaining in the polymer, and the recovery of the polymer is difficult by filtration and entails a special decantation device. Further, vacuum drying for the purpose of removing the organic solvent and other residual substances encounters difficulties because the polymer is significantly expanded to a large volume by the evaporation of the residual substances such as the organic solvent. The purified polymer obtained during the method 2), 3) or 4) is in the form of viscous liquid or mass even in the case where the polymer is precipitated by reprecipitation or the like. Thus, the direct drying of the polymer does not afford a polymer powder. In order to obtain the polymer as a powder, the method requires a special device such as a high-shear high-speed rotary device or a kneader to break the precipitated polymer by a shear force.

Other known techniques include 5) to dissolve polylactic acid in a solvent followed by cooling to induce phase separation and fractionation (Patent Literature 5), 6) to dissolve polylactic acid into a water-miscible organic solvent and to add an aqueous alkali metal salt solution to the solution (Patent Literature 6), and 7) to hydrolyze a high-molecular weight lactic acid polymer to precipitate a target lactic acid polymer (Patent Literature 7).

These conventional methods have difficulties in realizing industrial and simple production of a purified lactic acid-glycolic acid copolymer or a salt thereof in the form of powder, and are still susceptible to improvements.

CITATION LIST

Patent Literature

Patent Literature 1: Japanese Patent No. 3902518
Patent Literature 2: JP-B-S63-254128
Patent Literature 3: JP-A-2000-26588
Patent Literature 4: JP-A-H08-245779
Patent Literature 5: JP-A-2007-534803
Patent Literature 6: JP-A-2012-508293
Patent Literature 7: Japanese Patent No. 5046447

SUMMARY OF INVENTION

Technical Problem

An object of the invention is to produce a purified lactic acid-glycolic acid copolymer, preferably in the form of powder, having a reduced content of dimers such as residual lactide and glycolide by a simple industrial process without the use of any high-shear special device. Another object of the invention is to realize industrial simple production of a high-purity lactic acid-glycolic acid copolymer which has small amounts of dimers such as residual lactide and glycolide and small amounts of a low-molecular weight lactic acid-glycolic acid copolymer or a salt thereof and which has a small ratio of weight average molecular weight to number average molecular weight (Mw/Mn).

Solution to Problem

The present inventors carried out extensive studies to achieve the above objects. As a result, the present inventors have developed a process in which a specific solvent having a low solubility for a lactic acid-glycolic acid copolymer or a salt thereof is added to a solution of a lactic acid-glycolic acid copolymer or a salt thereof in a specific organic solvent, and the resultant solution with a reduced solubility for the copolymer is added to a specific solvent having a low solubility for a lactic acid-glycolic acid copolymer or a salt thereof typically by dropwise addition and preferably under stirring conditions. In this manner, surprisingly, the copolymer may be precipitated easily as a solid or preferably as a powder without the use of a special high-shear device and the content of dimers such as residual lactide and glycolide in the copolymer is sufficiently low. Preferably, the process involves treating the lactic acid-glycolic acid copolymer or the salt thereof under specific conditions using liquid-liquid phase separation. These configurations have been found to achieve the aforementioned objects. The present invention has been completed based on the findings.

Specifically, the present invention resides in the following [1] to [17].

[1] A process for producing a purified lactic acid-glycolic acid copolymer (A2) or a salt thereof including the steps of:

(1-1) dissolving a lactic acid-glycolic acid copolymer (A1) containing lactic acid units and glycolic acid units or a salt thereof into at least one organic solvent (B1) having a solubility at 25° C. of not less than 1 wt % to prepare a solution of the lactic acid-glycolic acid copolymer (A1) or the salt thereof;

(1-2) adding at least one solvent (S1) selected from water and aliphatic alcohols (B2) to the solution of the lactic acid-glycolic acid copolymer (A1) or the salt thereof to prepare a mixture liquid including the lactic acid-glycolic acid copolymer (A1) or the salt thereof;

(2) adding the mixture liquid prepared in the step (1-2) to a solvent (S2') including at least one selected from water and aliphatic alcohols (B2) to precipitate a purified lactic acid-glycolic acid copolymer (A2) or a salt thereof; and (3) recovering the precipitate of the purified lactic acid-glycolic acid copolymer (A2) or the salt thereof.

[2] The process for producing a purified lactic acid-glycolic acid copolymer (A2) or a salt thereof described in [1], wherein the lactic acid-glycolic acid copolymer (A1) contains 40 to 90 mol % of the lactic acid units and 60 to 10 mol % of the glycolic acid units (wherein the total of the lactic acid units and the glycolic acid units is 100 mol %).

[3] The process for producing a purified lactic acid-glycolic acid copolymer (A2) or a salt thereof described in [1] or [2], wherein the lactic acid-glycolic acid copolymer (A1) has a weight average molecular weight (Mw) in the range of 4,500 to 110,000.

[4] The process for producing a purified lactic acid-glycolic acid copolymer (A2) or a salt thereof described in any of [1] to [3], wherein in the step (1-1), the lactic acid-glycolic acid copolymer (A1) or the salt thereof is dissolved into the organic solvent (B1) with a concentration of 1 to 50 wt %.

[5] The process for producing a purified lactic acid-glycolic acid copolymer (A2) or a salt thereof described in any of [1] to [4], wherein the organic solvent (B1) used in the step (1-1) is an aprotic polar organic solvent.

[6] The process for producing a purified lactic acid-glycolic acid copolymer (A2) or a salt thereof described in any of [1] to [5], wherein the addition in the step (2) is dropwise addition.

[7] The process for producing a purified lactic acid-glycolic acid copolymer (A2) or a salt thereof described in any of [1] to [6], wherein in the step (2), the purified lactic acid-glycolic acid copolymer (A2) or the salt thereof is precipitated as a powder.

[8] The process for producing a purified lactic acid-glycolic acid copolymer (A2) or a salt thereof described in [1], wherein the process includes the steps of:

(1-1) dissolving a lactic acid-glycolic acid copolymer (A1) or a salt thereof into at least one organic solvent (B1) having a solubility at 25° C. of not less than 1 wt % to prepare a 1-50 wt % solution of the lactic acid-glycolic acid copolymer (A1) or the salt thereof, the lactic acid-glycolic acid copolymer (A1) containing 40 to 90 mol % of lactic acid units and 60 to 10 mol % of glycolic acid units (wherein the total of the lactic acid units and the glycolic acid units is 100 mol %) and having a weight average molecular weight (Mw) in the range of 4,500 to 110,000;

(1-2-A) adding at least one solvent (S1) selected from water and aliphatic alcohols (B2) to the solution of the lactic acid-glycolic acid copolymer (A1) or the salt thereof to prepare a mixture solution including the lactic acid-glycolic acid copolymer (A1) or the salt thereof;

(2) adding dropwise the mixture solution prepared in the step (1-2-A) to at least one solvent (S2) selected from water and aliphatic alcohols (B2) to precipitate a purified lactic acid-glycolic acid copolymer (A2) or a salt thereof as a powder; and (3) recovering the precipitate of the purified lactic acid-glycolic acid copolymer (A2) or the salt thereof.

[9] The process for producing a purified lactic acid-glycolic acid copolymer (A2) or a salt thereof described in any of [1] to [8], wherein the amount of the solvent (S1) used in the step (1-2) or (1-2-A) is 0.05 to 2.5 times by weight the amount of the organic solvent (B1).

[10] The process for producing a purified lactic acid-glycolic acid copolymer (A2) or a salt thereof described in any of [1] to [9], wherein the temperature of the solvent (S2') used in the step (2) is from the solidification point of the solvent (S2') to 25° C.

[11] The process for producing a purified lactic acid-glycolic acid copolymer (A2) or a salt thereof described in any of [1] to [10], wherein the amount of the solvent (S2') used in the step (2) is 3 or more times by weight the amount of the organic solvent (B1).

[12] The process described in any of [1] to [7], wherein the step (1-2) includes the following steps (1-2-B1) and (1-2-B2):

(1-2-B1) adding at least one solvent (B2) selected from water and aliphatic alcohols to the solution of the lactic acid-glycolic acid copolymer (A1) or the salt thereof and stirring the mixture to separate the mixture into two liquid phases; and (1-2-B2) recovering one of the two phases which includes the lactic acid-glycolic acid copolymer or the salt thereof having a larger weight average molecular weight (Mw).

[13] The process for producing a purified lactic acid-glycolic acid copolymer (A2) or a salt thereof described in [12], wherein the process includes the steps of:

(1-1) dissolving a lactic acid-glycolic acid copolymer (A1) or a salt thereof into at least one organic solvent (B1) having a solubility at 25° C. of not less than 10 wt % to prepare a 10-50 wt % solution of the lactic acid-glycolic acid copolymer (A1) or the salt thereof, the lactic acid-glycolic acid copolymer (A1) containing 40 to 90 mol % of lactic acid units and 60 to 10 mol % of glycolic acid units (wherein the total of the lactic acid units and the glycolic acid units is 100 mol %) and having a weight average molecular weight (Mw) in the range of 4,500 to 105,000;

(1-2-B1) adding at least one aliphatic alcohol (B2) to the solution of the lactic acid-glycolic acid copolymer (A1) or the salt thereof and stirring the mixture to separate the mixture into two liquid phases;

(1-2-B2) recovering one of the two phases which includes the lactic acid-glycolic acid copolymer or the salt thereof having a larger weight average molecular weight (Mw);

(2) adding dropwise the phase recovered in the step (1-2-B2) to a solvent including water to precipitate a purified lactic acid-glycolic acid copolymer (A2) or a salt thereof; and (3) recovering the precipitate of the purified lactic acid-glycolic acid copolymer (A2) or the salt thereof.

[14] The process for producing a purified lactic acid-glycolic acid copolymer (A2) or a salt thereof described in [13], wherein the solvent to which the recovered phase is added dropwise in the step (2) is water.

[15] The process for producing a purified lactic acid-glycolic acid copolymer (A2) or a salt thereof described in any of [12] to [14], wherein the phase recovered in the step (1-2-B2) is further subjected to one or more cycles of the steps (1-2-B1) and (1-2-B2) and thereafter subjected to the steps (2) and (3).

[16] The process for producing a purified lactic acid-glycolic acid copolymer (A2) or a salt thereof described in any of [12] to [15], wherein the organic solvent (B1) is added to the phase recovered in the step (1-2-B2) and thereafter the phase is further subjected to one or more cycles of the steps (1-2-B1) and (1-2-B2) and thereafter subjected to the steps (2) and (3).

[17] A sustained release formulation including a purified lactic acid-glycolic acid copolymer (A2) or a salt thereof obtained by the production process described in any of [1] to [16].

Advantageous Effects of Invention

According to the production processes of the invention, a powdery purified lactic acid-glycolic acid copolymer having a reduced content of dimers such as residual lactide and glycolide may be produced in a simple industrial manner without the use of any high-shear special device. Further, the production processes of the invention realize industrial simple production of a high-purity lactic acid-glycolic acid copolymer which has small amounts of dimers such as residual lactide and glycolide and small amounts of low-molecular weight lactic acid-glycolic acid polymers or salts thereof and which has a small ratio of weight average molecular weight to number average molecular weight (Mw/Mn). Lactic acid-glycolic acid copolymers produced by the processes are suited for applications such as sustained release formulations.

DESCRIPTION OF EMBODIMENTS

In the invention, a lactic acid-glycolic acid copolymer (A1) or a salt thereof is used as a raw material. The lactic acid-glycolic acid copolymer (A1) is a polymer containing lactic acid units and glycolic acid units. The lactic acid-glycolic acid copolymer (A1) usually contains the lactic acid units at 40 to 90 mol %, and preferably 50 to 85 mol % and the glycolic acid units at 60 to 10 mol %, and preferably 50 to 15 mol % (wherein the total of the lactic acid units and the glycolic acid units is 100 mol %). The lactic acid-glycolic acid copolymer (A1) may contain ester derivative units. Examples of the ester derivative units include monool residues, diol residues and polyol residues. These residues are derived from initiators (C) described later.

The weight average molecular weight (Mw) of the lactic acid-glycolic acid copolymer (A1) is usually 4,500 to 110,000, preferably 4,500 to 105,000, more preferably 5,000 to 90,300, still more preferably 5,000 to 80,000, and further preferably 8,000 to 80,000. The molecular weight distribution, namely, the weight average molecular weight/number average molecular weight (Mw/Mn) of the lactic acid-glycolic acid copolymer (A1) is usually 1.5 to 7.0, and preferably 1.8 to 6.0. It is also preferable that the Mw/Mn be 1.5 to 5.0, and particularly preferably 1.8 to 4.7. In the invention, the weight average molecular weight (Mw) and the weight average molecular weight/number average molecular weight (Mw/Mn) are values determined by gel permeation chromatography (GPC) relative to polystyrene standards.

For example, the lactic acid-glycolic acid copolymer (A1) may be produced by ring-opening polymerization of lactide that is a cyclic dimer of lactic acid and glycolide that is a cyclic dimer of glycolic acid as raw materials while optionally using additives such as an initiator (C) and a catalyst. Alternatively, the lactic acid-glycolic acid copolymer (A1) may be produced by copolymerizing lactic acid and glycolic acid optionally in the presence of a catalyst.

The initiator (C) may be a hydroxycarboxylic acid such as lactic acid or glycolic acid, in which case the obtainable molecule of the lactic acid-glycolic acid copolymer (A1) is terminated with a carboxyl group.

The initiator (C) may be a monool such as hexanol, octanol or dodecanol, in which case the obtainable lactic acid-glycolic acid copolymer (A1) has an ester derivative unit at an end of the molecule.

The initiator (C) may be a diol such as ethylene glycol or propylene glycol, in which case the obtainable lactic acid-glycolic acid copolymer (A1) includes an ester derivative unit in the inside of the molecule.

The initiator (C) may be a polyol such as glycerol, mannitol, pentaerythritol, sorbitol, xylitol, fructose, glucose or cyclodextrin, in which case the obtainable lactic acid-glycolic acid copolymer (A1) has a branched structure including an ester derivative unit in the inside of the molecule.

The lactic acid-glycolic acid copolymer (A1) produced as described above typically has a lactic acid content of 40 to 90 mol %, and more typically 50 to 85 mol %. In the lactic acid-glycolic acid copolymer (A1), the glycolic acid content is typically 60 to 10 mol %, and more typically 50 to 15 mol %. The lactic acid-glycolic acid copolymer (A1) may be a commercial product.

The lactic acid-glycolic acid copolymer (A1) may be in the form of salt. For example, the salt may be a salt of an inorganic metal, for example, an alkali metal such as sodium or potassium, or an alkaline earth metal such as calcium or magnesium, or may be a salt of a basic organic compound such as triethylamine.

[Step (1-1)]

In the step (1-1), the lactic acid-glycolic acid copolymer (A1) or the salt thereof is dissolved into at least one organic solvent (B1) having a solubility at 25° C. of not less than 1 wt % to give a solution of the lactic acid-glycolic acid copolymer or the salt thereof. Here, the term solubility means the solubility at 25° C. for a lactic acid-glycolic acid copolymer (containing 85 mol % lactic acid units and 15 mol % glycolic acid units) having a weight average molecular weight (Mw) of 76,000 and a number average molecular weight (Mn) of 14,100. In a preferred embodiment, the lactic acid-glycolic acid copolymer (A1) or the salt thereof is dissolved into at least one organic solvent (B1) having a solubility at 25° C. of not less than 10 wt % to give a solution of the lactic acid-glycolic acid copolymer or the salt thereof. Here, the term solubility in the phrase "solubility of not less than 10 wt %" means the solubility at 25° C. for a lactic acid-glycolic acid copolymer (containing 73 mol % lactic acid units and 27 mol % glycolic acid units) having a weight average molecular weight (Mw) of 11,300 and a number average molecular weight (Mn) of 5,300.

Examples of the organic solvents (B1) include aprotic polar organic solvents, in particular, aprotic polar organic solvents having 2 to 5 carbon atoms.

Examples of the aprotic polar organic solvents include ketones having 2 to 5 carbon atoms such as acetone; organic cyanides having 2 to 5 carbon atoms such as acetonitrile; cyclic ethers having 2 to 5 carbon atoms such as tetrahydrofuran; carboxylate esters having 2 to 5 carbon atoms such as ethyl acetate; amide compounds having 2 to 5 carbon atoms such as N,N-dimethylformamide; and sulfur-containing organic compounds having 2 to 5 carbon atoms such as dimethyl sulfoxide.

Of the organic solvents (B1), acetone, tetrahydrofuran and N,N-dimethylformamide are preferable from viewpoints such as easy handling. Acetone, tetrahydrofuran and N,N-dimethylformamide have a solubility at 25° C. of 30 wt % or above as measured with respect to a lactic acid-glycolic acid copolymer (containing 85 mol % lactic acid units and 15 mol % glycolic acid units) having a weight average molecular weight (Mw) of 76,000 and a number average molecular weight (Mn) of 14,100.

Of the organic solvents (B1), acetone and acetonitrile are particularly preferable from viewpoints such as easy handling. Acetone and acetonitrile have a solubility at 25° C. of 40 wt % or above as measured with respect to a lactic acid-glycolic acid copolymer (containing 73 mol % lactic acid units and 27 mol % glycolic acid units) having a weight average molecular weight (Mw) of 11,300 and a number average molecular weight (Mn) of 5,300.

Of the organic solvents (B1), acetone is particularly preferable from the viewpoint of toxicity in the event that the solvent remains in the purified lactic acid-glycolic acid copolymer (A2).

The concentration of the solution of the lactic acid-glycolic acid copolymer (A1) or the salt thereof may be controlled appropriately in accordance with factors such as the weight average molecular weight (Mw) and the molar ratio of the lactic acid units to the glycolic acid units of the lactic acid-glycolic acid copolymer (A1) that is used, so that the desired purified copolymer will be obtained, preferably in the form of powder. The concentration is usually in the range of 1 to 50 wt %, and may be, for example, 5 to 40 wt %. In an embodiment, the concentration of the solution of the lactic acid-glycolic acid copolymer or the salt thereof is usually in the range of 10 to 50 wt %. In a preferred embodiment, the concentration is preferably in the range of 20 to 40 wt % from viewpoints such as easy purification.

The copolymer or the salt thereof may be dissolved in the step (1-1) usually at a temperature of about 15 to 35° C., and preferably about 20 to 30° C. Where necessary, heating may be performed during the dissolution.

[Step (1-2)]

In the step (1-2), at least one solvent (S1) selected from water and aliphatic alcohols (B2) is added to the solution of the lactic acid-glycolic acid copolymer (A1) or the salt thereof obtained in the step (1-1), and a mixture liquid including the lactic acid-glycolic acid copolymer (A1) or the salt thereof is prepared. The mixture liquid may be formed by mixing the mixture of the solution from the step (1-1) and the solvent (S1) by stirring.

Examples of the aliphatic alcohols (B2) used in the step (1-2) include linear or branched aliphatic alcohols, in particular, those alcohols having 1 to 4 carbon atoms. Specific examples include methanol, ethanol, isopropyl alcohol, propyl alcohol and butyl alcohol.

The amount of the solvent (S1) used in the step (1-2) is preferably 0.05 to 2.5 times by weight, and more preferably 0.15 to 1.5 times by weight the amount of the organic solvent (B1).

The step (1-2-A), and the steps (1-2-B1) and (1-2-B2) described below represent preferred embodiments of the step (1-2).

[Step (1-2-A)]

In the step (1-2-A), at least one solvent (S1) selected from water and aliphatic alcohols (B2) is added to the solution of the lactic acid-glycolic acid copolymer (A1) or the salt thereof obtained in the step (1-1), and a mixture solution including the lactic acid-glycolic acid copolymer (A1) or the salt thereof is prepared. The mixture solution may be formed by mixing the mixture of the solution from the step (1-1) and the solvent (S1) by stirring.

Examples of the aliphatic alcohols (B2) used in the step (1-2-A) include the aliphatic alcohols mentioned in the section of the step (1-2). Of the aliphatic alcohols (B2), methanol, ethanol and isopropyl alcohol are preferable from viewpoints such as economic efficiency and odor. The aliphatic alcohols may be used singly or in combination with water, or two or more may be used in combination. In a preferred embodiment, water alone is used as the solvent (S1) from the viewpoints of economic efficiency and non-toxicity. The solvent (S1) should be miscible with the organic solvent (B1) used in the step (1-1).

In the step (1-2-A), the solvent (S1) may be mixed together with the solution of the lactic acid-glycolic acid copolymer (A1) or the salt thereof obtained in the step (1-1), usually at a temperature of about 15 to 35° C., and preferably about 20 to 30° C. Where necessary, heating may be performed during the mixing.

The amount of the solvent (S1) used in the step (1-2-A) is preferably 0.05 to 2.5 times by weight, and more preferably 0.15 to 1.5 times by weight the amount of the organic solvent (B1).

Mixing of the solvent (S1) with the solution of the lactic acid-glycolic acid copolymer (A1) or the salt thereof obtained in the step (1-1) results in a decrease of the solubility of the copolymer in the solution. As the solvent (51) is added in small portions to the solution obtained in the step (1-1), the mixture gradually becomes white turbid. At the addition of this amount which causes the onset of the occurrence of white turbidity, the mixture is in such a state that the copolymer is present in the solvent relatively stably while its solubility has been decreased to a degree. This configuration forms a relatively preferred embodiment of the mixture solution prepared in the step (1-2-A) of the invention. The addition of any larger amount of the solvent (S1) may result in the occurrence of liquid-liquid phase separation. Even in this case, the mixture may be used as such when heating of the mixture gives a uniform solution.

Hereinbelow, there will be described the steps (1-2-B1) and (1-2-B2) that represent another preferred embodiment of the step (1-2).

[Step (1-2-B1)]

In the step (1-2-B1), at least one aliphatic alcohol (B2) is added to the solution of the lactic acid-glycolic acid copolymer (A1) or the salt thereof obtained in the step (1-1), and stirring is performed to separate the mixture into two liquid phases.

Examples of the aliphatic alcohols (B2) used in the step (1-2-B1) include the aliphatic alcohols mentioned in the section of the step (1-2). Of the aliphatic alcohols (B2), ethanol and isopropyl alcohol are preferable for reasons such as that the purified lactic acid-glycolic acid copolymer or the salt thereof may be recovered in the form of powder. The aliphatic alcohols may be used singly, or two or more may be used in combination.

Separate liquid phases are formed in the step (1-2-B1). The solvent added in the step (1-2-B1) to induce the liquid-liquid phase separation may be selected appropriately in accordance with factors such as, for example, the weight average molecular weight (Mw) and the molar ratio of the lactic acid units to the glycolic acid units of the lactic acid-glycolic acid copolymer (A1) or the salt thereof used as the raw material, or the desired ratio of weight average molecular weight to number average molecular weight (Mw/Mn) of the purified lactic acid-glycolic acid copolymer (A2) or the salt thereof.

Preferably, the liquid phases formed in the step (1-2-B1) are clearly separate from each other with little intermediate phase. When, for example, the organic solvent (B1) used in the step (1-1) is acetone, the aliphatic alcohol (B2) in the step (1-2-B1) is preferably isopropyl alcohol or ethanol. When, for example, the organic solvent (B1) used in the step (1-1) is acetonitrile, the aliphatic alcohol (B2) is preferably isopropyl alcohol.

The weight ratio of the aliphatic alcohol (B2) to the organic solvent (B1) is not particularly limited as long as the liquid-liquid phase separation occurs in the step (1-2-B1), and may be determined appropriately in accordance with factors such as the weight average molecular weight (Mw) and the molar ratio of the lactic acid units to the glycolic acid units of the lactic acid-glycolic acid copolymer (A1) or the salt thereof. When, for example, the organic solvent (B1) is acetone and the aliphatic alcohol (B2) is isopropyl alcohol or ethanol, the weight ratio is usually not less than 0.6, and preferably not less than 0.70, and is usually not more than 3.5, and preferably not more than 2.5. When the organic solvent (B1) is acetonitrile and the aliphatic alcohol (B2) is isopropyl alcohol, the weight ratio is usually not less than 0.6, and preferably not less than 0.70, and is usually not more than 3.5, and preferably not more than 3.0.

If the weight ratio exceeds the upper limit, one of the separated phases, typically the lower phase tends to exhibit poor fluidity and the separation operation for the recovery of the phase may be difficult. If the weight ratio is less than the lower limit, the formation of separate liquid phases tends to be difficult.

In the step (1-2-B1), the formation of separate liquid phases usually takes place at a temperature of about 0 to 40° C., and preferably about 5 to 30° C., although variable depending on factors such as the weight average molecular weight (Mw) and the molar ratio of the lactic acid units to the glycolic acid units of the lactic acid-glycolic acid copolymer (A1) or the salt thereof used as the raw material.

The steps (1-1) and (1-2-B1) may be performed by simultaneously adding to the lactic acid-glycolic acid copolymer (A1) or the salt thereof the organic solvent (B1) in such an amount that the concentration prescribed in the step (1-1) is obtained and the aliphatic alcohol (B2) in such an amount that a desired weight ratio of the aliphatic alcohol (B2) to the organic solvent (B1) described in the step (1-2-B1) is obtained.

[Step (1-2-B2)]

In the step (1-2-B2), one of the two phases formed in the step (1-2-B1) which includes the lactic acid-glycolic acid copolymer or the salt thereof having a larger weight average molecular weight (Mw) is recovered. Of the two phases formed in the step (1-2-B1), the one which includes the lactic acid-glycolic acid copolymer or the salt thereof having a larger weight average molecular weight (Mw) may be easily identified by sampling the solutions of the respective phases and determining the weight average molecular weights (Mw) of the lactic acid-glycolic acid copolymer present in the respective phases.

Because the mixture has been separated into two liquid phases in the step (1-2-B1), the phase which includes the lactic acid-glycolic acid copolymer or the salt thereof having a larger weight average molecular weight (Mw) may be easily recovered by separation using a separatory funnel or the like.

In the case where one pass through the steps (1-1) and (1-2-B1) is insufficient for the lactic acid-glycolic acid copolymer or the salt thereof to attain desired properties, for example, a desired weight average molecular weight (Mw) and a desired weight average molecular weight/number average molecular weight (Mw/Mn), one or more cycles of the steps (1-2-B1) and (1-2-B2) may be performed after the step (1-2-B2). Alternatively, the organic solvent (B1) may be added to the recovered phase which includes the lactic acid-glycolic acid copolymer or the salt thereof having a larger weight average molecular weight (Mw), and thereafter the phase may be subjected to one or more cycles of the steps (1-2-B1) and (1-2-B2).

The step (1-2-B2) is usually performed at a temperature of about 0 to 30° C., and preferably about 5 to 25° C.

[Step (2)]

In the step (2), the mixture liquid prepared in the step (1-2) is added to a solvent (S2') including at least one selected from water and aliphatic alcohols (B2) to precipitate a purified lactic acid-glycolic acid copolymer (A2) or a salt thereof, preferably in the form of powder.

The solvent (S2') may include an organic solvent (B3) other than the aliphatic alcohols (B2). Examples of the organic solvents (B3) include aprotic polar organic solvents, in particular, aprotic polar organic solvents having 2 to 5 carbon atoms. Examples of the aprotic polar organic solvents include ketones having 2 to 5 carbon atoms such as acetone; organic cyanides having 2 to 5 carbon atoms such as acetonitrile; cyclic ethers having 2 to 5 carbon atoms such as tetrahydrofuran; carboxylate esters having 2 to 5 carbon atoms such as ethyl acetate; amide compounds having 2 to 5 carbon atoms such as N,N-dimethylformamide; and sulfur-containing organic compounds having 2 to 5 carbon atoms such as dimethyl sulfoxide.

The addition to the solvent (S2') may be performed continuously or intermittently. The addition is preferably dropwise addition. Particularly preferably, the mixture liquid is added as droplets. The addition time is not particularly limited, but is, for example, 0.05 to 20 hours, and preferably 0.3 to 3 hours. The rate of addition is not particularly limited. For example, the rate of addition, typically the dropping rate in the case of dropwise addition per unit amount of the solvent (S2') is 100 to 10000 g/hr/kg, and preferably 300 to 6000 g/hr/kg. The dropping rate in the case of the dropwise addition in droplets per unit amount of the solvent (S2') is 300 to 1000 g/hr/kg.

The temperature of the solvent (S2') used in the step (2) is preferably from the solidification point of the solvent (S2') to 25° C. If the temperature of the solvent (S2') exceeds 25° C., the copolymer that is precipitated tends to be in the form of viscous liquid or mass.

In the step (2), the solvent (S2') is preferably used in an amount that is 3 or more times by weight, more preferably 3 to 6 times by weight greater than the amount of the organic solvent (B1). The purified lactic acid-glycolic acid copolymer (A2) may be obtained in the form of powder even when the solvent (S2') is used in more than 6-fold amount by weight. However, such excessive use of the solvent is economically disadvantageous for reasons such as the need of large facilities. On the other hand, the use of less than 3-fold amount by weight of the solvent tends to result in the precipitation of a viscous liquid or massive copolymer.

In preferred embodiments, the step (2) described above is the step (2-A) or the step (2-B) described below.

In the case where the mixture liquid is prepared through the step (1-2-A), it is preferable that the step (2-A) described below be adopted. When the mixture liquid is prepared through the steps (1-2-B1) and (1-2-B2), the step (2-B) described below is preferably adopted.

[Step (2-A)]

In the step (2-A), the mixture liquid prepared in the step (1-2), typically the mixture solution prepared in the step (1-2-A) is added to, preferably by dropwise addition, at least one solvent (S2) selected from water and aliphatic alcohols (B2), and thereby a purified lactic acid-glycolic acid copolymer (A2) or a salt thereof is precipitated preferably in the form of powder. By the addition, preferably dropwise addition, of the mixture solution obtained through the step (1-2) to the solvent (S2), the purified lactic acid-glycolic acid copolymer (A2) or the salt thereof may be precipitated in the form of other than viscous liquid and preferably in the form of powder. This facilitates the post treatments such as recovery and drying. In addition, while the lactic acid-glycolic acid copolymer may contain any components having a very low molecular weight and having high affinity for the lactic acid-glycolic acid copolymer, for example, dimers such as lactide and glycolide and monomers such as lactic acid and glycolic acid resulting from the hydrolysis of these dimers, the solvent (S2) can dissolve these components out of the purified lactic acid-glycolic acid copolymer (A2) or the salt thereof.

Examples of the aliphatic alcohols (B2) used in the step (2-A) include linear or branched aliphatic alcohols, in particular, those alcohols having 1 to 4 carbon atoms. Specific examples include methanol, ethanol, isopropyl alcohol, propyl alcohol and butyl alcohol. The aliphatic alcohols may be used singly or in combination with water, or two or more may be used in combination. In a preferred embodiment, water alone is used as the solvent (S2) from the viewpoints of economic efficiency and nontoxicity. The solvent used here should be miscible with the organic solvent (B1) used in the step (1-1) and the solvent (S1) used in the step (1-2). Usually, the solvent (S2) used here is the same as the solvent (S1) used in the step (1-2). However, a different solvent may be used as long as it is miscible with the organic solvent (B1) and the solvent (S1). Of the solvents (S2), methanol, ethanol, isopropyl alcohol and water are preferable.

Methanol, ethanol and isopropyl alcohol can dissolve the dimers such as lactide and glycolide present in the lactic acid-glycolic acid copolymer (A1) and can also dissolve a lactic acid-glycolic acid copolymer having a low molecular weight. Thus, the use of these solvents as the solvents (S2) reduces the contents of a lactic acid-glycolic acid copolymer having a low molecular weight, and the obtainable purified lactic acid-glycolic acid copolymer (A2) is a high-purity copolymer having a narrow molecular weight distribution, namely, a small ratio of weight average molecular weight to number average molecular weight (Mw/Mn).

From viewpoints such as polymer powder quality and economic efficiency, the solvent (S2) is particularly preferably isopropyl alcohol or water. Because lactic acid-glycolic acid copolymers are not dissolved in water, the use of water as the solvent (S2) makes it possible to obtain a purified lactic acid-glycolic acid copolymer (A2) with a high yield.

In the step (2-A), the addition, preferably dropwise addition, of the mixture solution prepared in the step (1-2) to the solvent (S2) results in the instantaneous formation of a purified lactic acid-glycolic acid copolymer (A2) in the form of powder. The rate of addition in the case of dropwise addition is not particularly limited as long as the solution may be added as droplets.

In the step (2-A), a powdery copolymer may be obtained without the need of a high-shear device such as a homogenizer, by adding the mixture solution prepared in the step (1-2) to a device that is equipped with a stirrer commonly used in experimental facilities or industrial facilities (for example, a stirring blade such as an anchor stirring blade or a crescent stirring blade, or a rotating stirrer rod). For example, a powder of a purified lactic acid-glycolic acid copolymer (A2) may be obtained by adding the mixture solution, preferably by dropwise addition, to a device in which the solvent is being stirred under slow stirring conditions at 200 to 600 rpm and a tip speed of 0.7 to 2.0 m/s, preferably at 300 rpm and a tip speed of about 1 m/s.

The temperature of the solvent (S2) used in the step (2-A) is preferably from the solidification point of the solvent (S2) to 25° C. If the temperature of the solvent (S2) exceeds 25° C., the copolymer that is precipitated tends to be in the form of viscous liquid or mass.

In the step (2-A), the solvent (S2) is preferably used in an amount that is 3 or more times by weight, more preferably 3 to 6 times by weight greater than the amount of the organic solvent (B1). The purified lactic acid-glycolic acid copolymer (A2) may be obtained in the form of powder even when the solvent (S2) is used in more than 6-fold amount by weight. However, such excessive use of the solvent is economically disadvantageous for reasons such as the need of large facilities. On the other hand, the use of less than 3-fold amount by weight of the solvent tends to result in the precipitation of a viscous liquid or massive copolymer.

[Step (2-B)]

In the step (2-B), the mixture liquid prepared in the step (1-2), typically the phase, namely, the mixture solution recovered in the step (1-2-B2) is added to a solvent including water preferably by dropwise addition, and thereby a purified lactic acid-glycolic acid copolymer (A2) or a salt thereof is precipitated. Here, the solvent including water is typically water or a solvent including water and an organic solvent. Specifically, the solvent is water or includes water and at least one solvent (S3) selected from aliphatic alcohols (B2) and organic solvents (B3) other than the aliphatic alcohols (B2). This configuration allows the copolymer to be precipitated from the liquid obtained through the steps (1-1) and (1-2), preferably from the phase recovered through the steps (1-1), (1-2-B1) and (1-2-B2), into the solvent used in the step (2-B) while ensuring that the copolymer does not take the solvent of the recovered phase into the copolymer to form a gummy product. Consequently, the post treatments such as recovery and drying may be facilitated. In addition, while the copolymer may contain any components having a very low molecular weight and having high affinity for the copolymer, for example, dimers such as lactide and glycolide and monomers such as lactic acid and glycolic acid resulting from the hydrolysis of these dimers, the solvent including water can dissolve these components out of the purified lactic acid-glycolic acid copolymer (A2) or the salt thereof.

The solvent including water to which the recovered phase is added preferably by dropwise addition is usually used in an amount of 200 to 3000 parts by weight, and preferably 300 to 2000 parts by weight with respect to 100 parts by weight of the recovered phase in order to ensure that components with a very low molecular weight present in the lactic acid-glycolic acid copolymer (A2) will be removed efficiently.

The step (2-B) is usually performed at a temperature of about 0 to 30° C., and preferably about 5 to 25° C.

In order to efficiently remove low-molecular weight components such as monomer components present in the lactic acid-glycolic acid copolymer (A2), the solvent including water is preferably a solvent including 80 wt % to 100 wt % of water, and is more preferably water.

[Step (3)]

In the step (3), the purified lactic acid-glycolic acid copolymer (A2) or the salt thereof that has been precipitated in the step (2) is recovered. Because the purified lactic acid-glycolic acid copolymer (A2) or the salt thereof has been precipitated in the step (2) preferably in the form of powder, the precipitate may be easily recovered by a method such as filtration. Dimers such as residual lactide and glycolide that are dissolved in the solvent used may be discharged as the filtrate. Consequently, the purified lactic acid-glycolic acid copolymer (A2) or the salt thereof may achieve a reduction in the content of dimers such as lactide and glycolide.

The filtration method in the step (3) is not particularly limited, and examples thereof include vacuum filtration, pressure filtration and centrifugal filtration.

In the step (3), the precipitate may be washed with at least one solvent selected from water and aliphatic alcohols (B2) as required for purposes such as cleaning the purified lactic acid-glycolic acid copolymer (A2) of any residual materials such as the solvent and dimers such as residual lactide and glycolide attached to the precipitate. From the viewpoint of the freedom from organic solvents, the precipitate is preferably washed with water.

Examples of the washing methods include a slurry method in which a wet solid, typically a wet powder of the purified lactic acid-glycolic acid copolymer (A2) or the salt thereof precipitated in the step (2) is washed by being stirred in a washing liquid, and a rinsing method in which a washing liquid is passed through the precipitate. However, the washing methods are not limited thereto.

In the step (3), the purified lactic acid-glycolic acid copolymer (A2) is recovered as a solid or typically as a powder, and hence the copolymer may be dried under very low temperature conditions, for example, at 30 to 40° C. under a reduced pressure. Thus, it is very unlikely that drying causes the lactic acid-glycolic acid copolymer or the salt thereof to undergo undesired reactions such as pyrolysis and denaturation. Further, the fact that the polymer is a solid or is typically a powder makes it possible to efficiently remove by washing the organic solvent (B1) that is capable of dissolving the polymer. Consequently, the polymer may be easily dried while keeping the form of a solid or typically a powder, without being redissolved during drying or being expanded by the evaporation of the solvent.

The step (1-1) to the step (3) may be repeated in order to increase the purity of the purified lactic acid-glycolic acid copolymer (A2).

The purified lactic acid-glycolic acid copolymer (A2) obtained as described above usually contains 40 to 90 mol %, and preferably 50 to 85 mol % of the lactic acid units and usually contains 60 to 10 mol %, and preferably 50 to 15 mol % of the glycolic acid units (wherein the total of the lactic acid units and the glycolic acid units is 100 mol %). The weight average molecular weight (Mw) of the purified lactic acid-glycolic acid copolymer (A2) is usually in the range of 5,000 to 120,000, and preferably 8,000 to 85,000. The weight average molecular weight (Mw) of the purified lactic acid-glycolic acid copolymer (A2) may be preferably in the range of 6,000 to 95,000, and particularly preferably 6,500 to 90,000.

The Mw/Mn of the purified lactic acid-glycolic acid copolymer (A2) is usually in the range of 1.5 to 7.0, and preferably 1.8 to 6.0. The Mw/Mn of the purified lactic acid-glycolic acid copolymer (A2) may be usually in the range of 1.2 to 3.5, and preferably 1.2 to 3.2.

Further, the lactide content in the purified lactic acid-glycolic acid copolymer (A2) is usually not more than 0.6 wt %, and preferably not more than 0.1 wt %.

For example, this content may be decreased to 0.1 wt % or less by using methanol, ethanol, isopropyl alcohol or the like as the aliphatic alcohol (B2) in the step (2). The glycolide content in the purified lactic acid-glycolic acid copolymer (A2) is usually not more than 0.1 wt %.

The purified lactic acid-glycolic acid copolymer (A2) obtained by drying is preferably a powder in which particles with diameters of 1 mm or less represent 80 wt % or more of the whole particles and the maximum particle diameter is 3 mm or less. The average particle diameter of the purified lactic acid-glycolic acid copolymer (A2) is preferably not more than 0.5 mm.

In the case where the raw material is a salt of a lactic acid-glycolic acid copolymer (A1), the purified lactic acid-glycolic acid copolymer (A2) is obtained as the salt.

The purified lactic acid-glycolic acid copolymer (A2) or the salt thereof obtained according to the invention as described above has high purity and is suited for applications that require the high-purity lactic acid-glycolic acid copolymer (A2) or the salt thereof. For example, the purified lactic acid-glycolic acid copolymer (A2) or the salt thereof is suited for the production of sustained release formulations.

EXAMPLES

Hereinbelow, the present invention will be described in further detail based on Examples without limiting the scope of the invention to such Examples.

(1) GPC Measurement

In Examples and Comparative Examples below, the weight average molecular weight (Mw), the number average molecular weight (Mn) and the weight average molecular weight/number average molecular weight (Mw/Mn) were measured by gel permeation chromatography (GPC) under the following conditions.

Eluent: tetrahydrofuran
Columns: Shodex KF-806L×2 columns (manufactured by SHOWA DENKO K.K.)
Flow rate: 0.8 ml/min
Column temperature: 40° C.
Sample concentration: 0.3 wt %
Detector: RI detector (40° C.)

The calibration curve was prepared based on standard polystyrenes.

(2) GC Measurement

In Examples and Comparative Examples below, the contents of lactide and glycolide (dimers) were measured by gas chromatography (GC) under the following conditions.

Gas chromatograph: Shimadzu GC-14A (FID) fitted with heater or device with equivalent performance
Column: J & W DB-624 (60 m×0.53 mm ID)
Column temperature: 120° C.
Inlet temperature: 200° C.
Detector temperature: 230° C.
Carrier gas: helium (20 ml/min)
Carrier pressure: 0.13 MPa (1.3 kg/cm$^2$)
Combustible gas: hydrogen 0.11 MPa (1.1 kg/cm$^2$)
Air: 0.11 MPa (1.1 kg/cm$^2$)
Detector: hydrogen flame ionization detector (FID)
Amount injected: 3 μl
Split ratio: 2:1
Integrator: Shimadzu CR-6A or device with equivalent performance (3) Grain Size Distribution Measurement In Examples and Comparative Examples below, the grain size distribution was measured under the following conditions.

Sieve size: diameter 20 cm, height 4.5 cm
Sieve opening diameters: seven grades (5.6 mm, 2.8 mm, 2.0 mm, 1.0 mm, 0.35 mm, 0.18 mm and 0.106 mm)
Shaker: Ro-tap sieve shaker (RS-2 manufactured by TANAKA TECH CORPORATION)

Shaking conditions: A purified lactic acid-glycolic acid copolymer was placed on the sieve and shaken for 5 minutes at 100 taps/min.

After the completion of shaking through the sieve having any of the opening diameters, the weight of the purified lactic acid-glycolic acid copolymer retained on the sieve was measured, and the weight percentages of the respective grain sizes were calculated.

Example 1A

A 200 ml conical flask was loaded with 15 g of a lactic acid-glycolic acid copolymer having a weight average molecular weight (Mw) of 5,980 and a number average molecular weight (Mn) of 3,250 (lactic acid units:glycolic acid units molar ratio=75:25). The copolymer was dissolved with 85 g of acetone at 23 to 25° C. To the resultant solution, water was admixed in an amount of 21.3 g corresponding to 0.25 times by weight the amount of acetone at 23 to 25° C. Subsequently, a 1000 ml round-bottomed flask was loaded with 510 g of water corresponding to 6 times by weight the amount of acetone. The water was cooled to 5° C. while being stirred with a crescent stirring blade 7.5 cm in length at 300 rpm.

While maintaining the temperature and the rotational speed, the solution of the lactic acid-glycolic acid copolymer was added dropwise to the water with a roller pump over a period of about 1 hour. The dropping was accompanied by the precipitation of a powder of the lactic acid-glycolic acid copolymer.

Stirring was performed for about 1 hour, and thereafter the powdery lactic acid-glycolic acid copolymer was vacuum filtered on a glass filter to give a wet precipitate of the lactic acid-glycolic acid copolymer. The wet precipitate was rinsed by passing 100 g of water therethrough at 5° C. The resultant wet precipitate of the lactic acid-glycolic acid copolymer was vacuum dried at 30 to 40° C. to give a powder of the purified lactic acid-glycolic acid copolymer. Table 1A describes the yield, the weight average molecular weight/number average molecular weight (Mw/Mn), the contents of residual lactide and glycolide, and the grain size distribution of the purified lactic acid-glycolic acid copolymer. In Table 1A, the lactic acid-glycolic acid copolymer is abbreviated as PLGA.

Examples 2A to 8A

Purified lactic acid-glycolic acid copolymers were obtained as powders in the same manner as in Example 1A, except that the raw materials were changed to lactic acid-glycolic acid copolymers having Mw, Mn and a lactic acid unit to glycolic acid unit molar ratio described in the column of Raw PLGA in Table 1A, and that the conditions in the step (1-1) to the step (2) described in the column in Table 1A were adopted to prepare an organic solvent (B1) solution and a mixture solution in the step (1-2) and to precipitate the copolymer in the step (2). Table 1A describes the yields, the weight average molecular weight/number average molecular weight (Mw/Mn), the contents of residual lactide and glycolide, and the grain size distribution of the purified lactic acid-glycolic acid copolymers.

TABLE 1A

| | | Units | Ex. 1A | Ex. 2A | Ex. 3A | Ex. 4A | Ex. 5A |
|---|---|---|---|---|---|---|---|
| Raw PLGA (crude PLGA) quality | Lactic acid/glycolic acid molar ratio | mol/mol (%) | 75/25 | 77/23 | 74/26 | 51/49 | 74/26 |
| | Weight average molecular weight Mw | dalton | 5,980 | 7,720 | 11,400 | 13,000 | 14,800 |
| | Number average molecular weight Mn | dalton | 3,250 | 4,110 | 5,720 | 5,670 | 7,360 |
| | Weight average molecular weight Mw/Number average molecular weight Mn | — | 1.84 | 1.88 | 2.00 | 2.28 | 2.01 |
| | Residual monomers | | | | | | |
| | Lactide | wt % | 0.72 | 0.63 | 1.00 | 0.43 | 1.80 |
| | Glycolide | wt % | 0.06 | 0.08 | 0.10 | 0.22 | 0.10 |
| Conditions in step (1-1) to step (2) | Amount of PLGA | g | 15 | 15 | 15 | 15 | 15 |
| | Amount of acetone as organic solvent (B1) | g | 85.0 | 85.0 | 85.0 | 85.0 | 85.0 |
| | PLGA concentration | wt % | 15 | 15 | 15 | 15 | 15 |
| | Amount of water in step (1-2-A) | g | 21.3 | 21.3 | 17.0 | 17.0 | 17.0 |
| | | times/acetone | 0.25 | 0.25 | 0.20 | 0.20 | 0.20 |
| | Amount of water in step (2) | g | 510 | 510 | 510 | 510 | 510 |
| | | times/acetone | 6 | 6 | 6 | 6 | 6 |
| Yield and quality of purified PLGA | Amount of dry PLGA | g | 13.68 | 13.98 | 14.07 | 14.13 | 14.56 |
| | Yield | wt %/crude PLGA | 91.2 | 93.2 | 93.8 | 94.2 | 97.1 |
| | Weight average molecular weight Mw | dalton | 7,000 | 8,680 | 12,400 | 13,800 | 14,900 |
| | Number average molecular weight Mn | dalton | 4,450 | 5,200 | 6,630 | 5,730 | 7,700 |
| | Weight average molecular weight Mw/Number average molecular weight Mn | — | 1.57 | 1.67 | 1.87 | 2.41 | 1.93 |
| | Residual monomers | | | | | | |
| | Lactide | wt % | Below 0.01 | Below 0.01 | 0.11 | Below 0.01 | 0.28 |
| | Glycolide | wt % | Below 0.01 | Below 0.01 | Below 0.01 | Below 0.01 | Below 0.01 |
| Grain size distribution of purified PLGA | Sieve opening diameters | | | | | | |
| | 5.6 mm- | wt % | 0 | 0 | 0 | 0 | 0 |
| | 2.8 mm-5.6 mm | wt % | 0 | 0 | 0 | 0 | 0 |
| | 2.0 mm-2.8 mm | wt % | 0.5 | 0.3 | 0 | 0.9 | 0 |
| | 1.0 mm-2.0 mm | wt % | 9.7 | 10.6 | 4.5 | 13.7 | 0.8 |
| | 0.35 mm-1.0 mm | wt % | 47.8 | 41.3 | 32.9 | 41.7 | 31.2 |
| | 0.18 mm-0.35 mm | wt % | 28.3 | 21.1 | 18.4 | 20.1 | 20.8 |
| | 0.106 mm-0.18 mm | wt % | 9.4 | 16.0 | 19.7 | 13.7 | 21.4 |

TABLE 1A-continued

| | | | Ex. 6A | Ex. 7A | Ex. 8A |
|---|---|---|---|---|---|
| | -0.106 mm | wt % | 4.4 | 10.8 | 24.6 | 9.9 | 25.8 |

| | | Units | Ex. 6A | Ex. 7A | Ex. 8A |
|---|---|---|---|---|---|
| Raw PLGA (crude PLGA) quality | Lactic acid/glycolic acid molar ratio | mol/mol (%) | 85/15 | 74/27 | 74/27 |
| | Weight average molecular weight Mw | dalton | 76,000 | 80,000 | 109,600 |
| | Number average molecular weight Mn | dalton | 14,100 | 21,700 | 28,900 |
| | Weight average molecular weight Mw/ Number average molecular weight Mn | — | 5.40 | 3.69 | 3.79 |
| | Residual monomers | | | | |
| | Lactide | wt % | 1.40 | 0.70 | 1.10 |
| | Glycolide | wt % | 0.02 | 0.70 | 0.80 |
| Conditions in step (1-1) to step (2) | Amount of PLGA | g | 8 | 8 | 8 |
| | Amount of acetone as organic solvent (B1) | g | 125.3 | 125.3 | 125.3 |
| | PLGA concentration | wt % | 6 | 6 | 6 |
| | Amount of water in step (1-2-A) | g | 22.6 | 22.6 | 22.6 |
| | | times/acetone | 0.18 | 0.18 | 0.18 |
| | Amount of water in step (2) | g | 752 | 752 | 752 |
| | | times/acetone | 6 | 6 | 6 |
| Yield and quality of purified PLGA | Amount of dry PLGA | g | 7.62 | 7.50 | 7.52 |
| | Yield | wt %/crude PLGA | 95.3 | 93.8 | 94.0 |
| | Weight average molecular weight Mw | dalton | 76,200 | 82,200 | 109,000 |
| | Number average molecular weight Mn | dalton | 13,700 | 24,100 | 30,200 |
| | Weight average molecular weight Mw/ Number average molecular weight Mn | — | 5.55 | 3.42 | 3.61 |
| | Residual monomers | | | | |
| | Lactide | wt % | 0.18 | 0.08 | 0.10 |
| | Glycolide | wt % | Below 0.01 | Below 0.01 | Below 0.01 |
| Grain size distribution of purified PLGA | Sieve opening diameters | | | | |
| | 5.6 mm- | wt % | 0 | 0 | 0 |
| | 2.8 mm-5.6 mm | wt % | 0 | 0 | 0 |
| | 2.0 mm-2.8 mm | wt % | 0 | 1.5 | 0.9 |
| | 1.0 mm-2.0 mm | wt % | 1.5 | 3.8 | 11.3 |
| | 0.35 mm-1.0 mm | wt % | 29.3 | 9.5 | 27.2 |
| | 0.18 mm-0.35 mm | wt % | 35.9 | 35.7 | 34.8 |
| | 0.106 mm-0.18 mm | wt % | 18.3 | 22.1 | 13.8 |
| | -0.106 mm | wt % | 15.0 | 27.4 | 12.0 |

Example 9A

A 200 ml conical flask was loaded with 5 g of a lactic acid-glycolic acid copolymer having a weight average molecular weight (Mw) of 76,000, a number average molecular weight (Mn) of 14,100 and a weight average molecular weight/number average molecular weight (Mw/Mn) of 5.40 (lactic acid units:glycolic acid units molar ratio=85:15, residual lactide content 1.4 wt %, residual glycolide content 0.02 wt %). The copolymer was dissolved with 78.3 g of acetone at 23 to 25° C. To the resultant solution, water was admixed in an amount of 14.1 g corresponding to 0.18 times by weight the amount of acetone at 23 to 25° C. Subsequently, a 1000 ml round-bottomed flask was loaded with 470 g of methanol as an aliphatic alcohol (B2), the amount corresponding to 6 times by weight the amount of acetone. The methanol was cooled to 5° C. while being stirred with a crescent stirring blade 7.5 cm in length at 300 rpm.

While maintaining the temperature and the rotational speed, the solution of the lactic acid-glycolic acid copolymer was added dropwise to the methanol with a roller pump over a period of about 1 hour. The dropping was accompanied by the precipitation of a powder of the lactic acid-glycolic acid copolymer.

Stirring was performed for about 1 hour, and thereafter the powdery lactic acid-glycolic acid copolymer was vacuum filtered on a glass filter to give a wet precipitate of the lactic acid-glycolic acid copolymer. The wet precipitate was rinsed by passing 100 g of water therethrough at 5° C. The resultant wet precipitate of the lactic acid-glycolic acid copolymer was vacuum dried at 30 to 40° C. to give a powder of the purified lactic acid-glycolic acid copolymer. Table 2A describes the yield, the weight average molecular weight/number average molecular weight (Mw/Mn), and the contents of residual lactide and glycolide in the purified lactic acid-glycolic acid copolymer. In Table 2A, the lactic acid-glycolic acid copolymer is abbreviated as PLGA.

Examples 10A and 11A

Purified lactic acid-glycolic acid copolymers were obtained as powders in the same manner as in Example 9A, except that the solvent described in the column of Aliphatic alcohol (B2) in step (2) in Table 2A was used as the solvent (S2). Table 2A describes the yields, the weight average molecular weight/number average molecular weight (Mw/Mn), and the contents of residual lactide and glycolide in the purified lactic acid-glycolic acid copolymers.

TABLE 2A

|  |  |  | Ex. 9A | Ex. 10A | Ex. 11A |
|---|---|---|---|---|---|
| Yield and quality of purified PLGA | Aliphatic alcohol (B2) in step (2) | | Methanol | Ethanol | Isopropyl alcohol |
| | Amount of dry PLGA | g | 3.6 | 3.8 | 4.2 |
| | Yield | wt %/crude PLGA | 72.0 | 76.2 | 84.0 |
| | Weight average molecular weight Mw | dalton | 86,600 | 85,600 | 76,700 |
| | Number average molecular weight Mn | dalton | 37,800 | 31,400 | 27,000 |
| | Weight average molecular weight Mw/ Number average molecular weight Mn | — | 2.29 | 2.73 | 2.84 |
| | Residual monomers | | | | |
| | Lactide | wt % | 0.08 | Below 0.01 | Below 0.01 |
| | Glycolide | wt % | Below 0.01 | Below 0.01 | Below 0.01 |

Example 12A

Five 20 ml sample bottles were each loaded with 1 g of a lactic acid-glycolic acid copolymer having a weight average molecular weight (Mw) of 5,980 and a number average molecular weight (Mn) of 3,250 (lactic acid units:glycolic acid units molar ratio=75:25). The copolymer samples were dissolved with acetone at 23 to 25° C. so that the respective copolymer concentrations in the step (1-1) became 20 wt % (Test 12-1), 30 wt % (Test 12-2), 40 wt % (Test 12-3), 50 wt % (Test 12-4) and 60 wt % (Test 12-5). To each of the solutions, isopropyl alcohol was admixed in an amount equivalent to the amount of acetone by weight at 23 to 25° C. All the liquids having the respective concentrations were transparent. Subsequently, 35 g of water was added to a 50 ml conical flask and the water was cooled to 5° C. while a stirrer rod 2 cm in length was rotated at 600 rpm with a magnetic stirrer.

While maintaining the temperature and the rotational speed, the solution of the lactic acid-glycolic acid copolymer was added dropwise to the water with a pipette over a period of about 2 minutes. The system was observed to determine whether the precipitate of the lactic acid-glycolic acid copolymer was a powder. Each of the solutions having the concentrations for Tests 12-1 to 12-5 was dropped to the water in the separate experiment.

The precipitate was a 1 mm or finer powder when the concentration was 50 wt % or below (Tests 12-1 to 12-4), whilst the lactic acid-glycolic acid copolymer precipitated from the 60 wt % solution (Test 12-5) was spheres with a size of about 10 mm.

Example 13A 20 ml sample bottles were each loaded with 0.3 g of a lactic acid-glycolic acid copolymer having a weight average molecular weight (Mw) of 76,000 and a number average molecular weight (Mn) of 14,100 (lactic acid units:glycolic acid units molar ratio=85:15). The lactic acid-glycolic acid copolymer was dissolved with 4.7 g of acetone at 23 to 25° C. To each of the solutions, water was admixed in an amount of 1.2 g corresponding to 0.25 times by weight the amount of acetone at 23 to 25° C. With respect to six bottles containing the mixture liquid prepared in the above manner, the step (2) was performed at various temperatures.

Specifically, the experiment was carried out as follows. 30 g of water was added to 50 ml conical flasks. While rotating a stirrer rod 2 cm in length at 600 rpm with a magnetic stirrer, the water was brought to 5° C. (Test 13-1), 10° C. (Test 13-2), 15° C. (Test 13-3), 20° C. (Test 13-4) or 25° C. (Test 13-5). While maintaining the temperature and the rotational speed of the magnetic stirrer, the solution of the lactic acid-glycolic acid copolymer was added dropwise to the water with a pipette over a period of about 2 minutes. The system was observed to determine whether the precipitate of the lactic acid-glycolic acid copolymer was a powder. The solution was dropped to the water at the respective temperatures for Tests 13-1 to 13-5 in the separate experiment.

The copolymer was precipitated as a 1.5 mm or finer powder when the temperature of water was 25° C. or below (Tests 13-1 to 13-5), and the size of the powder was further reduced to 1.0 mm or less when the temperature of water was 15° C. or below (Tests 13-1 to 13-3).

Example 14A

A 20 ml sample bottle was loaded with 2 g of a lactic acid-glycolic acid copolymer having a weight average molecular weight (Mw) of 14,800, a number average molecular weight (Mn) of 7,360 and a weight average molecular weight/number average molecular weight (Mw/Mn) of 2.01 (lactic acid units:glycolic acid units molar ratio=74:26, residual lactide content 1.80 wt %, residual glycolide content 0.10 wt %). The copolymer was dissolved with 4.7 g of tetrahydrofuran as an organic solvent (B1) at 23 to 25° C. to give a 30 wt % solution. To the resultant solution, methanol as an aliphatic alcohol (B2) was admixed at 23 to 25° C. until white turbidity occurred. The amount added was 1.0 time by weight (4.7 g) the amount of tetrahydrofuran as the organic solvent (B1). Subsequently, a 50 ml conical flask was loaded with 33 g of water corresponding to 7 times by weight the amount of tetrahydrofuran as the organic solvent (B1). The water was cooled to 5° C. while rotating a stirrer rod 2 cm in length in the water at 600 rpm with a magnetic stirrer.

While maintaining the temperature and the rotational speed, the solution of the lactic acid-glycolic acid copolymer was added dropwise to the water with a pipette over a period of about 5 minutes. The dropping was accompanied by the precipitation of a powder of the lactic acid-glycolic acid copolymer.

Stirring was performed for about 30 minutes, and thereafter the powdery lactic acid-glycolic acid copolymer was vacuum filtered on a Kiriyama funnel with a diameter of 21 mm to give a wet precipitate of the lactic acid-glycolic acid copolymer. The wet precipitate was rinsed by passing 10 g of water therethrough at 5° C. The wet precipitate was vacuum dried together with the filter paper at 30 to 40° C. to ensure that the yield of the purified lactic acid-glycolic acid copolymer would be measured accurately. In this manner, a powder of the purified lactic acid-glycolic acid copolymer was obtained. Table 3A describes the yield (the dry weight was obtained by subtracting the weight of the filter paper from the total weight), the weight average molecular weight/number average molecular weight (Mw/Mn), and the contents of residual lactide and glycolide in the purified lactic acid-glycolic acid copolymer. In Table 3A, the lactic acid-glycolic acid copolymer is abbreviated as PLGA.

Examples 15A to 19A

Purified lactic acid-glycolic acid copolymers were obtained as powders in the same manner as in Example 14A, except that the organic solvent (B1) described in Table 3A was used in the step (1-1), and that the aliphatic alcohol (B2) described in Table 3A was used as the solvent (S1) in the step (1-2) in a weight ratio of the aliphatic alcohol (B2) described in Table 3A. Table 3A describes the yields, the weight average molecular weight/number average molecular weight (Mw/Mn), and the contents of residual lactide and glycolide in the purified lactic acid-glycolic acid copolymers.

Table 4A describes the yield, the weight average molecular weight/number average molecular weight (Mw/Mn), and the contents of residual lactide and glycolide in the purified lactic acid-glycolic acid copolymer. Because the dried product was foamed masses, the measurement of grain size distribution was omitted. In Table 4A, the lactic acid-glycolic acid copolymer is abbreviated as PLGA.

Comparative Example 2A

An attempt was made to prepare a purified lactic acid-glycolic acid copolymer by the same procedures as in Example 6A except that the step (1-2-A) was omitted.

When the solution of the lactic acid-glycolic acid copolymer obtained in the step (1-1) was dropped to water with a roller pump (the step (2)) without undergoing the step (1-2-A), the droplets added to water circulated as fibrous

TABLE 3A

| | | Units | Ex. 14A | Ex. 15A | Ex. 16A | Ex. 17A | Ex. 18A | Ex. 19A |
|---|---|---|---|---|---|---|---|---|
| Step (1-1) | Organic solvent (B1) | | Tetrahydrofuran | | | N,N-dimethylformamide | | |
| Step (1-2-A) | Aliphatic alcohol (B2) | | Methanol | Ethanol | Isopropyl alcohol | Methanol | Ethanol | Isopropyl alcohol |
| | Amount of aliphatic alcohol (B2) | times/organic solvent (B1) | 1.0 | 0.75 | 0.60 | 1.75 | 1.20 | 1.10 |
| Yield and quality of purified PLGA | Amount of dry PLGA | g | 1.92 | 1.90 | 1.85 | 1.91 | 1.94 | 1.95 |
| | Yield | wt %/crude PLGA | 96.0 | 95.0 | 92.5 | 95.5 | 97.0 | 97.5 |
| | Weight average molecular weight Mw | dalton | 15,100 | 15,300 | 16,000 | 15,300 | 15,000 | 15,100 |
| | Number average molecular weight Mn | dalton | 7,710 | 7,790 | 8,200 | 7,910 | 7,760 | 7,730 |
| | Weight average molecular weight Mw/ Number average molecular weight Mn | — | 1.96 | 1.96 | 1.95 | 1.93 | 1.94 | 1.95 |
| | Residual monomers | | | | | | | |
| | Lactide | wt % | 0.42 | 0.52 | 0.47 | 0.25 | 0.31 | 0.27 |
| | Glycolide | wt % | 0.03 | 0.07 | 0.05 | Below 0.01 | Below 0.01 | Below 0.01 |

Comparative Example 1A

An attempt was made to prepare a purified lactic acid-glycolic acid copolymer by the same procedures as in Example 5A except that the step (1-2) was omitted.

When the solution of the lactic acid-glycolic acid copolymer obtained in the step (1-1) was dropped to water with a roller pump (the step (2)) without undergoing the step (1-2-A), the droplets added to water circulated as viscous masses of the lactic acid-glycolic acid copolymer around the stirring blade. At the completion of the dropwise addition, the copolymer had formed viscous spherical masses with a size of about 5 cm.

After stirring was performed for about 1 hour, the spherical masses were scooped with a spoon, washed with 100 g of cold water at 5° C. on a glass filter, and vacuum filtered. Vacuum drying of the resultant spherical masses of the lactic acid-glycolic acid copolymer at 30 to 40° C. resulted in significant expansion.

masses of the lactic acid-glycolic acid copolymer around the stirring blade. At the completion of the dropwise addition, the fibrous masses around the stirring blade had grown to about 7 cm.

After stirring was performed for about 1 hour, the fibrous lactic acid-glycolic acid copolymer was vacuum filtered on a glass filter to give a wet fibrous precipitate of the lactic acid-glycolic acid copolymer. The wet precipitate was rinsed by passing 100 g of water therethrough at 5° C. The resultant wet precipitate of the lactic acid-glycolic acid copolymer was vacuum dried at 30 to 40° C. to give fibers of the purified lactic acid-glycolic acid copolymer.

Table 4A describes the yield, the weight average molecular weight/number average molecular weight (Mw/Mn), and the contents of residual lactide and glycolide in the purified lactic acid-glycolic acid copolymer.

TABLE 4A

| | | Units | Comp. Ex. 1A | Comp. Ex. 2A |
|---|---|---|---|---|
| Yield and quality of purified PLGA | Amount of dry PLGA | g | 14.54 | 7.75 |
| | Yield | wt %/crude PLGA | 96.9 | 96.9 |
| | Weight average molecular weight Mw | dalton | 14,700 | 78,900 |
| | Number average molecular weight Mn | dalton | 7,360 | 15,500 |
| | Weight average molecular weight Mw/ | — | 1.99 | 5.08 |

TABLE 4A-continued

| | | Units | Comp. Ex. 1A | Comp. Ex. 2A |
|---|---|---|---|---|
| | Number average molecular weight Mn | | | |
| | Residual monomers | | | |
| | Lactide | wt % | 1.05 | 0.80 |
| | Glycolide | wt % | 0.08 | 0.07 |
| Grain size | Sieve opening diameters | | | |
| distribution | 5.6 mm- | wt % | Not measured | 86.5 |
| of purified | 2.8 mm-5.6 mm | wt % | | 10.3 |
| PLGA | 2.0 mm-2.8 mm | wt % | | 1.2 |
| | 1.0 mm-2.0 mm | wt % | | 1.7 |
| | 0.35 mm-1.0 mm | wt % | | 0.3 |
| | 0.18 mm-0.35 mm | wt % | | 0 |
| | 0.106 mm-0.18 mm | wt % | | 0 |
| | -0.106 mm | wt % | | 0 |

Example 1B

At 20 to 25° C., 200 g of a lactic acid-glycolic acid copolymer having a weight average molecular weight (Mw) of 5680 and a number average molecular weight (Mn) of 2950 (lactic acid units:glycolic acid units molar ratio=75:25) was dissolved in 466 g of acetone. To the resultant solution, 466 g of isopropyl alcohol was added dropwise at 20 to 25° C. over a period of about 1 hour and the mixture was stirred at 20 to 25° C. for 0.5 hours.

After the stirring, the liquid obtained was allowed to stand at 5° C. for 4 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher weight average molecular weight. The liquid including the two liquid phases was transferred to a separatory funnel, and the lower phase liquid was recovered. Subsequently, over a period of about 2 hours while performing stirring, the lower phase recovered was added dropwise to five times by weight as much water that had been cooled to 5 to 10° C. as the amount of the lower phase, thereby precipitating the lactic acid-glycolic acid copolymer. Stirring was further performed at 5° C. for 10 hours. The powdery precipitate of the lactic acid-glycolic acid copolymer was vacuum filtered on a glass filter, and the precipitate of the lactic acid-glycolic acid copolymer was recovered. The precipitate was washed with approximately two times by weight as much water as the amount of the precipitate, and was vacuum dried at 30 to 40° C. to afford a purified lactic acid-glycolic acid copolymer. Table 1B describes the weight average molecular weight/number average molecular weight (Mw/Mn) and the molecular weight fractions (%) of the purified lactic acid-glycolic acid copolymer. In Table 1B, the lactic acid-glycolic acid copolymer is abbreviated as PLGA.

Example 2B

At 20 to 25° C., 200 g of a lactic acid-glycolic acid copolymer having Mw, Mn and a lactic acid unit to glycolic acid unit molar ratio described in the column of Example 2B in Table 1B was dissolved in 466 g of acetone. To the resultant solution, 466 g of isopropyl alcohol was added dropwise at 20 to 25° C. over a period of about 1 hour and the mixture was stirred at 20 to 25° C. for 0.5 hours.

After the stirring, the liquid obtained was allowed to stand at 5° C. for 4 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher weight average molecular weight. The liquid including the two liquid phases was transferred to a separatory funnel, and the lower phase liquid was recovered. Subsequently, over a period of about 2 hours while performing stirring, the lower phase recovered was added dropwise to five times by weight as much water that had been cooled to 5 to 10° C. as the amount of the lower phase, thereby precipitating the lactic acid-glycolic acid copolymer. Stirring was further performed at 5° C. for 10 hours. The powdery precipitate of the lactic acid-glycolic acid copolymer was vacuum filtered on a glass filter, and the precipitate of the lactic acid-glycolic acid copolymer was recovered. The precipitate was washed with approximately two times by weight as much water as the amount of the precipitate, and was vacuum dried at 30 to 40° C. to afford a purified lactic acid-glycolic acid copolymer. Table 1B describes the weight average molecular weight/number average molecular weight (Mw/Mn), the molecular weight fractions (%), and the contents (wt %) of residual lactide and glycolide in the purified lactic acid-glycolic acid copolymer.

Examples 3B to 5B

At 20 to 25° C., 200 g of a lactic acid-glycolic acid copolymer having Mw, Mn and a lactic acid unit to glycolic acid unit molar ratio described in any of the columns of Examples 3B to 5B in Table 1B was dissolved in 466 g of acetone. To the resultant solution, 466 g of isopropyl alcohol was added dropwise at 20 to 25° C. over a period of about 1 hour and the mixture was stirred at 20 to 25° C. for 0.5 hours.

After the stirring, the liquid obtained was allowed to stand at 20 to 25° C. for 2 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher weight average molecular weight. The liquid including the two liquid phases was transferred to a separatory funnel, and the lower phase liquid was recovered. Subsequently, over a period of about 1 hour while performing stirring, the lower phase recovered was added dropwise to five times by weight as much water that had been cooled to 5 to 10° C. as the amount of the lower phase, thereby precipitating the lactic acid-glycolic acid copolymer. Stirring was further performed at 5° C. for 4 hours. The powdery precipitate of the lactic acid-glycolic acid copolymer was vacuum filtered on a glass filter, and the precipitate of the lactic acid-glycolic acid copolymer was recovered. The precipitate was washed with approximately two times by weight as much water as the amount of the precipitate, and was vacuum dried at 30 to 40° C. to afford a purified lactic acid-glycolic acid copolymer. Table 1B describes the weight average molecular weight/number average molecular weight (Mw/Mn), the molecular weight fractions (%), and the contents (wt %) of residual lactide and glycolide in the purified lactic acid-glycolic acid copolymer.

Example 6B

At 20 to 25° C., 200 g of a lactic acid-glycolic acid copolymer (lactic acid units:glycolic acid units molar ratio=85:15) having Mw of 73,200, Mn of 23,300 and Mw/Mn of 3.14 described in the column of Example 6B in Table 1B was dissolved in 800 g of acetone. To the resultant solution, 600 g of isopropyl alcohol was added dropwise at 20 to 25° C. over a period of about 1 hour and the mixture was stirred at 20 to 25° C. for 1 hour.

After the stirring, the liquid obtained was allowed to stand at 20 to 25° C. for 1 hour and was separated into two liquid phases including an upper phase and a lower phase. Thereafter, small amounts of the respective phases were sampled and analyzed by GPC. The measurement showed that the lactic acid-glycolic acid copolymer in the lower phase had a higher weight average molecular weight. The liquid including the two liquid phases was transferred to a separatory funnel, and the lower phase liquid was recovered. Subsequently, over a period of about 2 hours while dispersing the droplets with a homogenizer, the lower phase recovered was added dropwise to twelve times by weight as much water that had been controlled at 20 to 25° C. as the amount of the lower phase. Further, stirring was performed at 20 to 25° C. for 1 hour. The powdery precipitate of the lactic acid-glycolic acid copolymer was vacuum filtered on a glass filter, and the precipitate of the lactic acid-glycolic acid copolymer was recovered. The precipitate was washed with approximately two times by weight as much water as the amount of the precipitate, and was vacuum dried at 30 to 40° C. to afford a purified lactic acid-glycolic acid copolymer. Table 1B describes the weight average molecular weight/number average molecular weight (Mw/Mn), the molecular weight fractions (%), and the contents (wt %) of residual lactide and glycolide in the purified lactic acid-glycolic acid copolymer.

TABLE 1B

| | | Ex. 1B | Ex. 2B | Ex. 3B | Ex. 4B | Ex. 5B | Ex. 6B |
|---|---|---|---|---|---|---|---|
| Quality of PLGA (before purification) | Lactic acid/glycolic acid molar ratio | 75/25 | 77/23 | 73/27 | 73/27 | 73/27 | 85/15 |
| | Weight average molecular weight Mw | 5,680 | 6,880 | 9,640 | 11,300 | 13,900 | 73,200 |
| | Number average molecular weight Mn | 2,950 | 3,480 | 4,680 | 5,300 | 6,290 | 23,300 |
| | Weight average molecular weight Mw/ Number average molecular weight Mn | 1.93 | 1.98 | 2.06 | 2.15 | 2.21 | 3.14 |
| | Molecular weight fractions (%) | | | | | | |
| | 40,000- | 0 | 0 | 0.5 | 1.1 | 2.9 | 69.5 |
| | 16,000-40,000 | 2.2 | 5.1 | 14.2 | 14.2 | 20.4 | 21.5 |
| | 5,000-16,000 | 45.4 | 52.6 | 57.7 | 57.7 | 56.1 | 6.2 |
| | 2,000-4,000 | 24.4 | 19.6 | 12.5 | 12.5 | 9.9 | 0.9 |
| | 500-1,500 | 9.1 | 6.9 | 5.2 | 4.2 | 3.6 | 1.2 |
| | Residual monomers (%) | | | | | | |
| | Lactide | 0.72 | 0.70 | 0.88 | 1.36 | 1.80 | 1.40 |
| | Glycolide | 0.06 | 0.08 | 0.12 | 0.38 | 0.10 | 0.02 |
| Recovery rate | Recovery rate (%) | 28 | 37 | 45 | 48 | 59 | 72 |
| Quality of PLGA (after purification) | Weight average molecular weight Mw | 7,180 | 8,960 | 12,400 | 14,700 | 15,900 | 81,200 |
| | Number average molecular weight Mn | 4,760 | 5,470 | 7,190 | 8,000 | 8,560 | 33,900 |
| | Weight average molecular weight Mw/ Number average molecular weight Mn | 1.51 | 1.63 | 1.72 | 1.84 | 1.86 | 2.39 |
| | Molecular weight fractions (%) | | | | | | |
| | 40,000- | 0 | 0.1 | 0.9 | 2.3 | 3.7 | 77.2 |
| | 16,000-40,000 | 3.4 | 9.4 | 23.7 | 31.9 | 34.8 | 17.7 |
| | 5,000-16,000 | 63.4 | 66.8 | 61.6 | 55.2 | 51.5 | 3.6 |
| | 2,000-4,000 | 16 | 10.9 | 6.2 | 4.5 | 4.3 | 0.4 |
| | 500-1,500 | 2.6 | 2.4 | 1.6 | 1.5 | 1.3 | 0.6 |
| | Residual monomers (%) | | | | | | |
| | Lactide | 0.05 | 0.08 | 0.04 | 0.10 | — | 0.08 |
| | Glycolide | Below 0.01% | Below 0.01% | Below 0.01% | Below 0.01% | — | Below 0.01% |

Example 7B

At 20 to 25° C., 40 g of a lactic acid-glycolic acid copolymer (lactic acid units:glycolic acid units molar ratio=85:15) having Mw of 68,800, Mn of 14,980 and Mw/Mn of 4.54 was dissolved in 160 g of acetone. To the resultant solution, 120 g of isopropyl alcohol corresponding to 0.75 times by weight the amount of acetone was added dropwise over a period of about 0.5 hours while performing stirring. After the stirring, the liquid obtained was allowed to stand at 20 to 25° C. for 2 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher molecular weight. The liquid including the two liquid phases was transferred to a separatory funnel, and the lower phase liquid was recovered. Subsequently, over a period of about 1 hour while dispersing the droplets with a homogenizer, the lower phase recovered was added dropwise to twelve times by weight as much water that had been controlled at 20° C. as the amount of the lower phase, thereby precipitating the lactic acid-glycolic acid copolymer. The powdery precipitate of the lactic acid-glycolic acid copolymer was vacuum filtered on a glass filter, and the precipitate of the lactic acid-glycolic acid copolymer was recovered. The precipitate was washed with approximately three times by weight as much water as the amount of the precipitate, and was vacuum dried at 30 to 40° C. to afford a purified lactic acid-glycolic acid copolymer. Table 2B describes the weight average molecular weight/number average molecular weight (Mw/Mn), the molecular weight fractions (%), and the contents (wt %) of residual lactide and glycolide in the purified lactic acid-glycolic acid copolymer. In Table 2B, the lactic acid-glycolic acid copolymer is abbreviated as PLGA.

Example 8B

At 20 to 25° C., 40 g of a lactic acid-glycolic acid copolymer (lactic acid units:glycolic acid units molar ratio=85:15) having Mw of 68,800, Mn of 14,980 and Mw/Mn of 4.54 was dissolved in 160 g of acetone. To the resultant solution, 120 g of isopropyl alcohol corresponding to 0.75 times by weight the amount of acetone was added dropwise over a period of about 0.5 hours while performing stirring. After the stirring, the liquid obtained was allowed to stand at 20 to 25° C. for 2 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher molecular weight. The liquid including the two liquid phases was transferred to a separatory funnel, and the lower phase liquid was recovered. While performing stirring, 80 g of acetone and 61 g of isopropyl alcohol were added dropwise to 170 g of the lower phase recovered. Further, stirring was performed at 20 to 25° C. for 1 hour. The resultant liquid was allowed to stand for 2 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher molecular weight. The liquid including the two liquid phases was transferred to a separatory funnel, and the lower phase liquid was recovered. Subsequently, over a period of about 1 hour while dispersing the droplets with a homogenizer, the lower phase recovered was added dropwise to twelve times by weight as much water that had been controlled at 20° C. as the amount of the lower phase, thereby precipitating the lactic acid-glycolic acid copolymer. The powdery precipitate of the lactic acid-glycolic acid copolymer was vacuum filtered on a glass filter, and the precipitate of the lactic acid-glycolic acid copolymer was recovered. The precipitate was washed with approximately three times by weight as much water as the amount of the precipitate, and was vacuum dried at 30 to 40° C. to afford a purified lactic acid-glycolic acid copolymer. Table 2B describes the weight average molecular weight/number average molecular weight (Mw/Mn), the molecular weight fractions (%), and the contents (wt %) of residual lactide and glycolide in the purified lactic acid-glycolic acid copolymer.

Comparative Example 1B

At 20 to 25° C., 40 g of a lactic acid-glycolic acid copolymer (lactic acid units:glycolic acid units molar ratio=85:15) having Mw of 68,800, Mn of 14,980 and Mw/Mn of 4.54 was dissolved in 160 g of acetone. The resultant solution was added dropwise to twelve times by weight as much water as the amount of the solution that had been controlled at 20° C. over a period of about 1 hour while dispersing the droplets with a homogenizer, thereby precipitating the lactic acid-glycolic acid copolymer. The powdery precipitate of the lactic acid-glycolic acid copolymer was vacuum filtered on a glass filter, and the precipitate of the lactic acid-glycolic acid copolymer was recovered. The precipitate was washed with approximately three times by weight as much water as the amount of the precipitate, and was vacuum dried at 30 to 40° C. to afford a purified lactic acid-glycolic acid copolymer. Table 2B describes the weight average molecular weight/number average molecular weight (Mw/Mn), the molecular weight fractions (%), and the contents (wt %) of residual lactide and glycolide in the purified lactic acid-glycolic acid copolymer.

TABLE 2B

| | | Ex. 7B | Ex. 8B | Comp. Ex. 1B |
|---|---|---|---|---|
| Quality of PLGA (before purification) | Weight average molecular weight Mw | 68,800 | 68,800 | 68,800 |
| | Number average molecular weight Mn | 14,980 | 14,980 | 14,980 |
| | Weight average molecular weight Mw/ Number average molecular weight Mn | 4.54 | 4.54 | 4.54 |
| | Molecular weight fractions (%) | | | |
| | 40,000- | 65.4 | 65.4 | 65.4 |
| | 16,000-40,000 | 22.6 | 22.6 | 22.6 |
| | 5,000-16,000 | 7.4 | 7.4 | 7.4 |
| | 2,000-4,000 | 1.34 | 1.34 | 1.34 |
| | 500-1,500 | 1.6 | 1.6 | 1.6 |
| | Residual monomers (%) | | | |
| | Lactide | 1.40 | 1.40 | 1.40 |
| | Glycolide | 0.02 | 0.02 | 0.02 |
| | Organic solvent | Acetone | Acetone | Acetone |
| | Aliphatic alcohol | Isopropyl alcohol | Isopropyl alcohol | Not added |
| | Number of separation operations performed | 1 | 2 | 0 |

TABLE 2B-continued

|  |  | Ex. 7B | Ex. 8B | Comp. Ex. 1B |
|---|---|---|---|---|
| Quality of PLGA (after purification) | Weight average molecular weight Mw | 78,200 | 84,800 | 70,700 |
|  | Number average molecular weight Mn | 26,350 | 36,280 | 17,530 |
|  | Weight average molecular weight Mw/ Number average molecular weight Mn | 2.96 | 2.33 | 4.03 |
|  | Molecular weight fractions (%) |  |  |  |
|  | 40,000- | 74.8 | 80.5 | 67.3 |
|  | 16,000-40,000 | 19.0 | 15.8 | 22.0 |
|  | 5,000-16,000 | 4.1 | 2.5 | 6.8 |
|  | 2,000-4,000 | 0.6 | 0.4 | 1.2 |
|  | 500-1,500 | 0.7 | 0.3 | 1.4 |
|  | Residual monomers (%) |  |  |  |
|  | Lactide | 0.09 | 0.05 | 0.13 |
|  | Glycolide | Below 0.01% | Below 0.01% | Below 0.01% |

Reference Examples 1B to 3B

At 20 to 25° C., 5 g of a lactic acid-glycolic acid copolymer (lactic acid units:glycolic acid units molar ratio=75:25) having Mw of 11,300, Mn of 5,300 and Mw/Mn of 2.15 was dissolved in 11.7 g of acetone. To the resultant solution, isopropyl alcohol was added dropwise in a weight ratio to acetone described in Table 3B below (Reference Example 1B: 1.0 time by weight (11.7 g), Reference Example 2B: 1.5 times by weight (17.5 g), Reference Example 3B: 2.0 times by weight (23.4 g)) over a period of about 0.5 hours. The mixture was stirred at 20 to 25° C. for 0.5 hours.

After the stirring, the resultant liquid was allowed to stand at 20 to 25° C. for 5 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher weight average molecular weight. The liquid including the two liquid phases was transferred to a separatory funnel, and the lower phase liquid was recovered. The lower phase recovered was distilled to remove the organic solvent, thereby obtaining a purified lactic acid-glycolic acid copolymer in the form of viscous liquid. Table 3B describes the weight average molecular weight/number average molecular weight (Mw/Mn) and the molecular weight fractions (%) of the purified lactic acid-glycolic acid copolymer. In Table 3B, the lactic acid-glycolic acid copolymer is abbreviated as PLGA.

Reference Examples 4B to 6B

At 20 to 25° C., 5 g of a lactic acid-glycolic acid copolymer (lactic acid units:glycolic acid units molar ratio=75:25) having Mw of 11,300, Mn of 5,300 and Mw/Mn of 2.15 was dissolved in 11.7 g of acetone. To the resultant solution, ethanol was added dropwise in a weight ratio to acetone described in Table 3B below (Reference Example 4B: 1.0 time by weight (11.7 g), Reference Example 5B: 1.5 times by weight (17.5 g), Reference Example 6B: 2.0 times by weight (23.4 g)) over a period of about 0.5 hours. The mixture was stirred at 20 to 25° C. for 0.5 hours.

After the stirring, the resultant liquid was allowed to stand at 20 to 25° C. for 5 hours and was separated into two liquid phases including an upper phase and a lower phase. Thereafter, small amounts of the respective phases were sampled and analyzed by GPC. The measurement showed that the lactic acid-glycolic acid copolymer in the lower phase had a higher weight average molecular weight. The liquid including the two liquid phases was transferred to a separatory funnel, and the lower phase liquid was recovered. The lower phase recovered was distilled to remove the organic solvent, thereby obtaining a purified lactic acid-glycolic acid copolymer in the form of viscous liquid. Table 3B describes the weight average molecular weight/number average molecular weight (Mw/Mn) and the molecular weight fractions (%) of the purified lactic acid-glycolic acid copolymer.

TABLE 3B

|  |  | Ref. Ex. 1B | Ref. Ex. 2B | Ref. Ex. 3B | Ref. Ex. 4B | Ref. Ex. 5B | Ref. Ex. 6B |
|---|---|---|---|---|---|---|---|
| Quality of PLGA (before purification) | Weight average molecular weight Mw | 11,300 | 11,300 | 11,300 | 11,300 | 11,300 | 11,300 |
|  | Number average molecular weight Mn | 5,300 | 5,300 | 5,300 | 5,300 | 5,300 | 5,300 |
|  | Weight average molecular weight Mw/ Number average molecular weight Mn | 2.15 | 2.15 | 2.15 | 2.15 | 2.15 | 2.15 |
|  | Molecular weight fractions (%) |  |  |  |  |  |  |
|  | 40,000- | 1.1 | 1.1 | 1.1 | 1.1 | 1.1 | 1.1 |
|  | 16,000-40,000 | 20.4 | 20.4 | 20.4 | 20.4 | 20.4 | 20.4 |
|  | 5,000-16,000 | 56.1 | 56.1 | 56.1 | 56.1 | 56.1 | 56.1 |
|  | 2,000-4,000 | 9.9 | 9.9 | 9.9 | 9.9 | 9.9 | 9.9 |
|  | 500-1,500 | 3.6 | 3.6 | 3.6 | 3.6 | 3.6 | 3.6 |
|  | Organic solvent | Acetone | Acetone | Acetone | Acetone | Acetone | Acetone |
|  | Aliphatic alcohol | Isopropyl alcohol | Isopropyl alcohol | Isopropyl alcohol | Ethanol | Ethanol | Ethanol |

TABLE 3B-continued

|  |  | Ref. Ex. 1B | Ref. Ex. 2B | Ref. Ex. 3B | Ref. Ex. 4B | Ref. Ex. 5B | Ref. Ex. 6B |
|---|---|---|---|---|---|---|---|
|  | Aliphatic alcohol/Organic solvent (weight ratio) | 1.0 | 1.5 | 2.0 | 1.0 | 1.5 | 2.0 |
|  | Separation of two phases | Good | Good | Good | Good | Good | Good |
| Quality of PLGA (after purification) | Weight average molecular weight Mw | 13,800 | 12,800 | 12,400 | 14,400 | 13,200 | 12,700 |
|  | Number average molecular weight Mn | 7,590 | 7,470 | 7,240 | 7,860 | 7,820 | 7,570 |
|  | Weight average molecular weight Mw/ Number average molecular weight Mn | 1.82 | 1.71 | 1.71 | 1.83 | 1.69 | 1.68 |
|  | Molecular weight fractions (%) |  |  |  |  |  |  |
|  | 40,000- | 1.6 | 1.4 | 1.3 | 2.1 | 1.5 | 1.3 |
|  | 16,000-40,000 | 28.8 | 24.4 | 22.9 | 31.2 | 25.6 | 23.7 |
|  | 5,000-16,000 | 57.9 | 61.8 | 62.0 | 55.5 | 61.7 | 62.4 |
|  | 2,000-4,000 | 5.0 | 5.3 | 6.0 | 4.8 | 4.8 | 5.4 |
|  | 500-1,500 | 1.6 | 1.3 | 1.4 | 1.5 | 1.2 | 1.2 |

Reference Example 7B

At 20 to 25° C., 5 g of a lactic acid-glycolic acid copolymer (lactic acid units:glycolic acid units molar ratio=75:25) having Mw of 11,300, Mn of 5,300 and Mw/Mn of 2.15 was dissolved in 11.7 g of acetone. To the resultant solution, 0.5 times by weight as much isopropyl alcohol as the amount of acetone was added dropwise over a period of about 0.5 hours while performing stirring. After the stirring, the resultant liquid was allowed to stand at 20 to 25° C. for 5 hours but liquid-liquid phase separation did not occur.

Reference Example 8B

At 20 to 25° C., 5 g of a lactic acid-glycolic acid copolymer (lactic acid units:glycolic acid units molar ratio=75:25) having Mw of 11,300, Mn of 5,300 and Mw/Mn of 2.15 was dissolved in 11.7 g of acetone. To the resultant solution, 4.0 times by weight as much isopropyl alcohol as the amount of acetone was added dropwise over a period of about 0.5 hours while performing stirring. The solution was allowed to stand at 20 to 25° C. for 5 hours and was separated into two liquid phases. However, the lower phase had so high viscosity that the separation operation was difficult.

Reference Example 9B

At 20 to 25° C., 5 g of a lactic acid-glycolic acid copolymer (lactic acid units:glycolic acid units molar ratio=75:25) having Mw of 11,300, Mn of 5,300 and Mw/Mn of 2.15 was dissolved in 11.7 g of acetone. To the resultant solution, 0.5 times by weight as much ethanol as the amount of acetone was added dropwise over a period of about 0.5 hours while performing stirring. After the stirring, the resultant liquid was allowed to stand at 20 to 25° C. for 5 hours but liquid-liquid phase separation did not occur.

Reference Example 10B

At 20 to 25° C., 5 g of a lactic acid-glycolic acid copolymer (lactic acid units:glycolic acid units molar ratio=75:25) having Mw of 11,300, Mn of 5,300 and Mw/Mn of 2.15 was dissolved in 11.7 g of acetone. To the resultant solution, 4.0 times by weight as much ethanol as the amount of acetone was added dropwise over a period of about 0.5 hours while performing stirring. After the stirring, the resultant liquid was allowed to stand at 20 to 25° C. for 5 hours and was separated into two liquid phases. However, the lower phase had so high viscosity that the separation operation was difficult.

INDUSTRIAL APPLICABILITY

According to the present invention, purified lactic acid-glycolic acid copolymers or salts thereof useful as, for example, materials for sustained release formulations, may be produced in an easy industrial manner while controlling the contents of dimers such as residual lactide and glycolide and the contents of low-molecular weight lactic acid-glycolic acid polymers or salts thereof.

CROSS-REFERENCE TO RELATED APPLICATIONS

The present application claims priority from Japanese Patent Applications Nos. 2013-082988 and 2014-020184, the entire contents of which are incorporated herein by reference.

The invention claimed is:
1. A process for producing a purified lactic acid-glycolic acid copolymer (A2) or a salt thereof comprising the steps of:
   (1-1) dissolving a lactic acid-glycolic acid copolymer (A1) containing lactic acid units and glycolic acid units or a salt thereof into at least one organic solvent (B1) having a solubility at 25° C. of not less than 1 wt % to prepare a solution of the lactic acid-glycolic acid copolymer (A1) or the salt thereof;
   (1-2) adding at least one solvent (S1) selected from water and aliphatic alcohols (B2) to the solution of the lactic acid-glycolic acid copolymer (A1) or the salt thereof to prepare a second solution including the lactic acid-glycolic acid copolymer (A1) or the salt thereof, the organic solvent (B1) and the at least one solvent (S1);
   (2) adding the second solution prepared in the step (1-2) to a solvent (S2') including at least one selected from water and aliphatic alcohols (B2) to precipitate a purified lactic acid-glycolic acid copolymer (A2) or a salt thereof; and
   (3) recovering the precipitate of the purified lactic acid-glycolic acid copolymer (A2) or the salt thereof.
2. The process for producing a purified lactic acid-glycolic acid copolymer (A2) or a salt thereof according to claim 1, wherein the lactic acid-glycolic acid copolymer (A1) contains 40 to 90 mol % of the lactic acid units and 60 to 10 mol % of the glycolic acid units (wherein the total of the lactic acid units and the glycolic acid units is 100 mol %).

3. The process for producing a purified lactic acid-glycolic acid copolymer (A2) or a salt thereof according to claim 1, wherein the lactic acid-glycolic acid copolymer (A1) has a weight average molecular weight (Mw) in the range of 4,500 to 110,000.

4. The process for producing a purified lactic acid-glycolic acid copolymer (A2) or a salt thereof according to claim 1, wherein in the step (1-1), the lactic acid-glycolic acid copolymer (A1) or the salt thereof is dissolved into the organic solvent (B1) with a concentration of 1 to 50 wt %.

5. The process for producing a purified lactic acid-glycolic acid copolymer (A2) or a salt thereof according to claim 1, wherein the organic solvent (B1) used in the step (1-1) is an aprotic polar organic solvent.

6. The process for producing a purified lactic acid-glycolic acid copolymer (A2) or a salt thereof according to claim 1, wherein the addition in the step (2) is dropwise addition.

7. The process for producing a purified lactic acid-glycolic acid copolymer (A2) or a salt thereof according to claim 1, wherein in the step (2), the purified lactic acid-glycolic acid copolymer (A2) or the salt thereof is precipitated as a powder.

8. The process for producing a purified lactic acid-glycolic acid copolymer (A2) or a salt thereof according to claim 1, wherein the process comprises the steps of:
(1-1) dissolving a lactic acid-glycolic acid copolymer (A1) or a salt thereof into at least one organic solvent (B1) having a solubility at 25° C. of not less than 1 wt % to prepare a 1-50 wt % solution of the lactic acid-glycolic acid copolymer (A1) or the salt thereof, the lactic acid-glycolic acid copolymer (A1) containing 40 to 90 mol % of lactic acid units and 60 to 10 mol % of glycolic acid units (wherein the total of the lactic acid units and the glycolic acid units is 100 mol %) and having a weight average molecular weight (Mw) in the range of 4,500 to 110,000;
(1-2-A) adding at least one solvent (S1) selected from water and aliphatic alcohols (B2) to the solution of the lactic acid-glycolic acid copolymer (A1) or the salt thereof to prepare a second solution including the lactic acid-glycolic acid copolymer (A1) or the salt thereof, the organic solvent (B1) and the at least one solvent (S1);
(2) adding dropwise the second solution prepared in the step (1-2-A) to at least one solvent (S2) selected from water and aliphatic alcohols (B2) to precipitate a purified lactic acid-glycolic acid copolymer (A2) or a salt thereof as a powder; and
(3) recovering the precipitate of the purified lactic acid-glycolic acid copolymer (A2) or the salt thereof.

9. The process for producing a purified lactic acid-glycolic acid copolymer (A2) or a salt thereof according to claim 1, wherein the amount of the solvent (S1) used in the step (1-2) is 0.05 to 2.5 times by weight the amount of the organic solvent (B1).

10. The process for producing a purified lactic acid-glycolic acid copolymer (A2) or a salt thereof according to claim 1, wherein the temperature of the solvent (S2') used in the step (2) is from the solidification point of the solvent (S2') to 25° C.

11. The process for producing a purified lactic acid-glycolic acid copolymer (A2) or a salt thereof according to claim 1, wherein the amount of the solvent (S2') used in the step (2) is 3 or more times by weight the amount of the organic solvent (B1).

12. A process for producing a purified lactic acid-glycolic acid copolymer (A2) or a salt thereof comprising the steps of:
(1-1) dissolving a lactic acid-glycolic acid copolymer (A1) containing lactic acid units and glycolic acid units or a salt thereof into at least one organic solvent (B1) having a solubility at 25° C. of not less than 1 wt % to prepare a solution of the lactic acid-glycolic acid copolymer (A1) or the salt thereof;
(1-2-B1) adding at least one solvent (B2) selected from water and aliphatic alcohols to the solution of the lactic acid-glycolic acid copolymer (A1) or the salt thereof and stirring the mixture to separate the mixture into two liquid phases; and
(1-2-B2) recovering one of the two phases which includes the lactic acid-glycolic acid copolymer or the salt thereof having a larger weight average molecular weight (Mw)
(2) adding the phase recovered in the step (1-2-B2) to a solvent including at least one selected from water and aliphatic alcohols to precipitate a purified lactic acid-glycolic acid (A2) or a salt thereof; and
(3) recovering the precipitate of the purified lactic acid-glycolic acid copolymer (A2) or the salt thereof.

13. The process for producing a purified lactic acid-glycolic acid copolymer (A2) or a salt thereof according to claim 12, wherein the process comprises the steps of:
(1-1) dissolving a lactic acid-glycolic acid copolymer (A1) or a salt thereof into at least one organic solvent (B1) having a solubility at 25° C. of not less than 10 wt % to prepare a 10-50 wt % solution of the lactic acid-glycolic acid copolymer (A1) or the salt thereof, the lactic acid-glycolic acid copolymer (A1) containing 40 to 90 mol % of lactic acid units and 60 to 10 mol % of glycolic acid units (wherein the total of the lactic acid units and the glycolic acid units is 100 mol %) and having a weight average molecular weight (Mw) in the range of 4,500 to 105,000;
(1-2-B1) adding at least one aliphatic alcohol (B2) to the solution of the lactic acid-glycolic acid copolymer (A1) or the salt thereof and stirring the mixture to separate the mixture into two liquid phases;
(1-2-B2) recovering one of the two phases which includes the lactic acid-glycolic acid copolymer or the salt thereof having a larger weight average molecular weight (Mw);
(2) adding dropwise the phase recovered in the step (1-2-B2) to a solvent including water to precipitate a purified lactic acid-glycolic acid (A2) or a salt thereof; and
(3) recovering the precipitate of the purified lactic acid-glycolic acid copolymer (A2) or the salt thereof.

14. The process for producing a purified lactic acid-glycolic acid copolymer (A2) or a salt thereof according to claim 13, wherein the solvent to which the recovered phase is added dropwise in the step (2) is only water.

15. The process for producing a purified lactic acid-glycolic acid copolymer (A2) or a salt thereof according to claim 12, wherein the phase recovered in the step (1-2-B2) is further subjected to one or more cycles of the steps (1-2-B1) and (1-2-B2) and thereafter subjected to the steps (2) and (3).

16. The process for producing a purified lactic acid-glycolic acid copolymer (A2) or a salt thereof according to claim 12, wherein the organic solvent (B1) is added to the phase recovered in the step (1-2-B2) and thereafter the phase is further subjected to one or more cycles of the steps (1-2-B1) and (1-2-B2) and thereafter subjected to the steps (2) and (3).

\* \* \* \* \*